(12) United States Patent
Davis et al.

(10) Patent No.: US 10,772,751 B2
(45) Date of Patent: Sep. 15, 2020

(54) FENESTRATED ENDOLUMINAL PROSTHESIS AND SYSTEM AND METHOD OF DEPLOYMENT THEREOF

(71) Applicant: Cook Medical Technologies LLC, Bloomington, IN (US)

(72) Inventors: Brandon J. Davis, Fishers, IN (US); Jarin A. Kratzberg, Lafayette, IN (US); Blayne A. Roeder, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 184 days.

(21) Appl. No.: 15/695,409

(22) Filed: Sep. 5, 2017

(65) Prior Publication Data

US 2018/0071124 A1    Mar. 15, 2018

Related U.S. Application Data

(60) Provisional application No. 62/385,578, filed on Sep. 9, 2016.

(51) Int. Cl.
*A61F 2/962* (2013.01)
*A61F 2/06* (2013.01)
(Continued)

(52) U.S. Cl.
CPC ............... *A61F 2/962* (2013.01); *A61F 2/06* (2013.01); *A61F 2/07* (2013.01); *A61F 2/954* (2013.01);
(Continued)

(58) Field of Classification Search
CPC .. A61F 2/89; A61F 2/954; A61F 2/962; A61F 2002/061; A61F 2002/075; A61F 2002/9511
See application file for complete search history.

(56) References Cited

U.S. PATENT DOCUMENTS 5,380,304 A    1/1995   Parker
5,554,183 A    9/1996   Nazari
(Continued)

FOREIGN PATENT DOCUMENTS

EP    2517671 A2    10/2012

OTHER PUBLICATIONS

Office Action for European Application No. 17275139.8 dated Jan. 16, 2018, 3 pages.
(Continued)

*Primary Examiner* — Martin T Ton
(74) *Attorney, Agent, or Firm* — Brinks Gilson & Lione

(57) ABSTRACT

The present embodiments provide an endoluminal prosthesis deployment system and method for deploying the prosthesis for cannulation of branch vessels. The prosthesis includes an anterior fenestration and a posterior opening. A guide is disposed to exit the prosthesis lumen through a lateral fenestration, enter through the anterior fenestration, and exit the prosthesis lumen through the posterior opening. A sheath can be preloaded over the branch wire at the lateral fenestration for vessel cannulation, such as in renal arteries. The sheath can include another branch wire that extends from the lateral fenestration to another lateral fenestration. An end of the guide is retracted after partial expansion of the prosthesis, and another sheath is inserted over the retracted guide and moved through the posterior opening and to the anterior fenestration. A separate branch guide wire is then directed through the sheath for vessel cannulation, such as the SMA.

22 Claims, 14 Drawing Sheets

(51) Int. Cl.
  *A61F 2/07* (2013.01)
  *A61F 2/954* (2013.01)
  *A61F 2/95* (2013.01)
  *A61F 2/89* (2013.01)

(52) U.S. Cl.
  CPC ............ *A61F 2/89* (2013.01); *A61F 2002/061* (2013.01); *A61F 2002/075* (2013.01); *A61F 2002/9511* (2013.01)

(56) References Cited

U.S. PATENT DOCUMENTS

| | | |
|---|---|---|
| 5,800,521 A | 9/1998 | Orth |
| 6,416,499 B2 | 7/2002 | Paul, Jr. |
| 6,524,335 B1 | 2/2003 | Hartley et al. |
| 6,589,227 B2 | 7/2003 | Sønderskov Klint |
| 6,918,925 B2 | 7/2005 | Tehrani |
| 7,025,758 B2 | 4/2006 | Klint |
| 7,335,224 B2 | 2/2008 | Øhlenschlæger |
| 7,435,253 B1 | 10/2008 | Hartley et al. |
| 7,537,606 B2 | 5/2009 | Hartley et al. |
| 7,611,529 B2 | 11/2009 | Greenberg et al. |
| 7,651,519 B2 | 1/2010 | Dittman |
| 7,722,657 B2 | 5/2010 | Hartley |
| 7,758,626 B2 | 7/2010 | Kim et al. |
| 7,867,270 B2 | 1/2011 | Hartley et al. |
| 7,976,575 B2 | 7/2011 | Hartley |
| 8,043,354 B2 | 10/2011 | Greenberg et al. |
| 8,123,796 B2 | 2/2012 | Kasprzak |
| 8,292,951 B2 | 10/2012 | Muzslay |
| 8,480,726 B2 | 7/2013 | Cunningham et al. |
| 8,636,789 B2 | 1/2014 | Ivancev et al. |
| 8,709,061 B2 | 4/2014 | Greenberg et al. |
| 8,747,455 B2 | 6/2014 | Greenberg |
| 8,945,202 B2 | 2/2015 | Mayberry et al. |
| 8,974,518 B2 | 3/2015 | Bruszewski et al. |
| 9,101,455 B2 | 8/2015 | Roeder et al. |
| 9,149,382 B2 | 10/2015 | Desai et al. |
| 2001/0034514 A1 | 10/2001 | Parker |
| 2002/0032408 A1 | 3/2002 | Parker et al. |
| 2004/0230287 A1 | 11/2004 | Hartley et al. |
| 2005/0171479 A1 | 8/2005 | Hruska et al. |
| 2006/0004433 A1 | 1/2006 | Greenberg et al. |
| 2006/0155302 A1 | 7/2006 | Sisken et al. |
| 2007/0043425 A1 | 2/2007 | Hartley et al. |
| 2007/0078395 A1 | 4/2007 | Valaie |
| 2007/0244547 A1 | 10/2007 | Greenan |
| 2008/0294234 A1 | 11/2008 | Hartley et al. |
| 2012/0041535 A1 | 2/2012 | Huser et al. |
| 2012/0041544 A1 | 2/2012 | Wolf |
| 2013/0046371 A1* | 2/2013 | Greenberg ................ A61F 2/07 623/1.11 |
| 2013/0079870 A1 | 3/2013 | Roeder et al. |
| 2013/0123907 A1* | 5/2013 | Roeder ..................... A61F 2/06 623/1.23 |
| 2014/0155983 A1 | 6/2014 | Beane et al. |
| 2015/0082595 A1 | 3/2015 | King |

OTHER PUBLICATIONS

Partial European Search Report for European Application No. 17275139.8 dated Apr. 20, 2018, 8 pages.

Examination Report for European Application No. 17275139.8 dated Apr. 15, 2020, 6 pages.

\* cited by examiner

FENESTRATED ENDOLUMINAL PROSTHESIS AND SYSTEM AND METHOD OF DEPLOYMENT THEREOF

RELATED APPLICATIONS

This application claims the benefit of the filing date under 35 U.S.C. § 119(e) of Provisional U.S. Patent Application Ser. No. 62/385,578, filed Sep. 9, 2016, which is incorporated by reference in its entirety.

BACKGROUND

The present disclosure relates generally to medical devices. More particularly, it relates to a fenestrated endoluminal device and system and method of deployment for implantation within a human or animal body for repair of damaged vessels, ducts, or other physiological pathways.

Using endoluminal devices, such as stent grafts, to treat aneurysms is common in the medical field. Stent grafts are deployed by accessing a vasculature with a small incision in the skin and guiding a delivery system to the target area. This intraluminal delivery is less invasive and generally preferred over more intrusive forms of surgery. Multiple stent grafts may be implanted using intraluminal delivery to provide a system of interconnected stent grafts.

At times, the aneurysm has engulfed a main vessel and branch vessels extending from the main vessel. In these cases, it may be necessary to deploy one or more stent grafts in a major vessel (e.g., the aorta) at or near an intersecting branch vessel (e.g., innominate, carotid, subclavian, celiac, SMA, and renal arteries). In these cases, a stent graft may be provided with one or more fenestrations so that the stent graft can overlap the branch vessels without blocking flow to these vessels. Once the stent graft is placed in the main vessel, it may be necessary to provide interventional access between the main vessel and a branch vessel. For example, a physician may desire to deliver additional interventional catheter devices carrying balloons, stents, grafts, imaging devices, and the like through the fenestration.

However, before such a catheter device can be delivered through the fenestration to a target vessel, a guide wire must be provided and delivered through the fenestration to the target vessel. Typically, this requires multiple steps. First, the physician must deliver and navigate a set of catheters and wires to pass a guide wire through the fenestration. Once the fenestration is cannulated, the physician must then deliver and navigate a separate set of catheters and wires to pass a guide wire into the target vessel. These procedures are labor intensive, involve manipulating multiple wires in a vessel at the same time, and depend heavily on the skill of the physician to cannulate both the fenestration and the target vessel. The steps become even more complicated and numerous when the physician needs to cannulate more than one fenestration and more than one target vessel. In addition, the complexity of the procedure increases as the number of cannulating wires increases, since the physician must take precaution to ensure that the multiple wire ends do not become entangled, or that they do not inadvertently contact and damage the prosthesis or a vessel wall. When the branch vessels are the renal arteries and the SMA, there are additional challenges. The physician will need to withdraw the sheath entirely via a contralateral sheath. Afterwards, the SMA is manually cannulated via a contralateral sheath. The renal arteries are then cannulated following SMA cannulation.

SUMMARY

The present embodiments provide an endoluminal prosthesis deployment system including a prosthesis and a guide. The prosthesis includes a support structure coupled to a graft body. The prosthesis includes a first end opening, a second end opening, and a lumen extending longitudinally between the first and second end openings. An anterior fenestration is disposed in a sidewall of the graft body of the prosthesis below the first end opening. At least one lateral fenestration is disposed in the sidewall below the anterior fenestration and circumferentially spaced from the anterior fenestration. The lateral fenestration is configured to receive a secondary graft. An opening is disposed in the sidewall below the lateral fenestration and substantially longitudinally aligned with the anterior fenestration. The guide is arranged extending from below the second end opening and through the lumen to the lateral fenestration, exiting the lateral fenestration, traversing along an exterior surface of the prosthesis, entering the anterior fenestration, longitudinally traversing along an interior surface of the prosthesis, and exiting the opening to extend away from the opening toward the second end opening of the prosthesis.

In one embodiment, a method for deploying a prosthesis within a main vessel of a patient, having a branch vessel intersecting the main vessel. The method includes one or more of the following steps. A step includes providing a prosthesis and a guide. The prosthesis includes a first end opening, a second end opening, and a prosthesis lumen extending longitudinally between the first and second end openings. An anterior fenestration is disposed in a sidewall of a graft body of the prosthesis below the first end opening. An opening is disposed in the sidewall closer in proximity to the second end opening than the anterior fenestration. A lateral fenestration is disposed in the sidewall in between the anterior fenestration and the opening. The guide is arranged extending from below the second end opening, extending through the lumen to the lateral fenestration, exiting the lateral fenestration, traversing along an exterior surface of the prosthesis, entering the anterior fenestration, longitudinally traversing along an interior surface of the prosthesis, and exiting the opening to extend away from the opening toward the second end opening of the prosthesis. A step includes expanding a portion of the prosthesis that includes the anterior fenestration, the opening, and the lateral fenestration within a main vessel such that the anterior fenestration is in alignment with a branch vessel. A step includes coupling a snare device to an end of the guide exiting the opening. A step includes retracting the end of the guide away from the second end opening of the prosthesis.

In another embodiment, an endoluminal prosthesis deployment system is provided, including a prosthesis and a guide. The prosthesis includes a tubular graft body, a first axial end opening, a second axial end opening, a lumen extending longitudinally between the first and second axial end openings. A first fenestration is defined in a sidewall of the graft body of the prosthesis below the first axial end opening along a posterior circumferential region of the prosthesis. A second fenestration is defined in the sidewall below the first fenestration and along a lateral circumferential region circumferentially spaced from the posterior circumferential region. An opening is defined in the sidewall below the second fenestration and along a posterior circumferential region circumferentially spaced from the posterior circumferential region and the lateral circumferential region. The prosthesis includes a patch coupled to the sidewall of the graft body, and disposed to cover the opening. The guide extends from below the second axial end opening, extending through the lumen to the second fenestration, exiting the second fenestration, traversing along an exterior surface of the prosthesis, entering the first fenestration, longitudinally traversing along an interior surface of the prosthesis, and exiting the opening and traversing away from the opening between the patch and exterior surface of the prosthesis toward the second axial end opening of the prosthesis.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

DETAILED DESCRIPTION OF THE PREFERRED EMBODIMENTS

In the present application, the term "proximal" when referring to a delivery device refers to a direction that is farthest away from an operator using a delivery device, while the term "distal" refers to a direction that is generally closest to the operator using the delivery device. The proximal and distal ends of a delivery device may also be referred to as an introduction end of the delivery device and an operator end of the delivery device, respectively. The term "operator end" of the delivery device is that portion of the device that is intended to remain outside of a patient during a procedure. The term "introduction end" of the delivery device, which is opposite to the operator end, is that portion of the device that is intended to be inserted within a patient during a procedure. When referring to the prosthesis itself relative to the delivery device, the proximal end of the prosthesis is that part of the prosthesis closest in proximity to the introduction end of the delivery device and the distal end of the prosthesis is that end that is closest in proximity to the operator end of the delivery device. When referring to the prosthesis relative to placement in the human body of the patient, the ends of the various devices and parts of devices may be referred to as the inflow end (that end that receives fluid first, and the outflow end (that end from which the fluid exits). The term "ipsilateral" is used to indicate that the diseased vessel(s) being accessed during a given procedure are on the same side of the body (right or left) as the vascular access delivery system/introducer, while "contralateral" signifies that the vessel(s) of interest are on the opposite side of the body.

Figure 1:
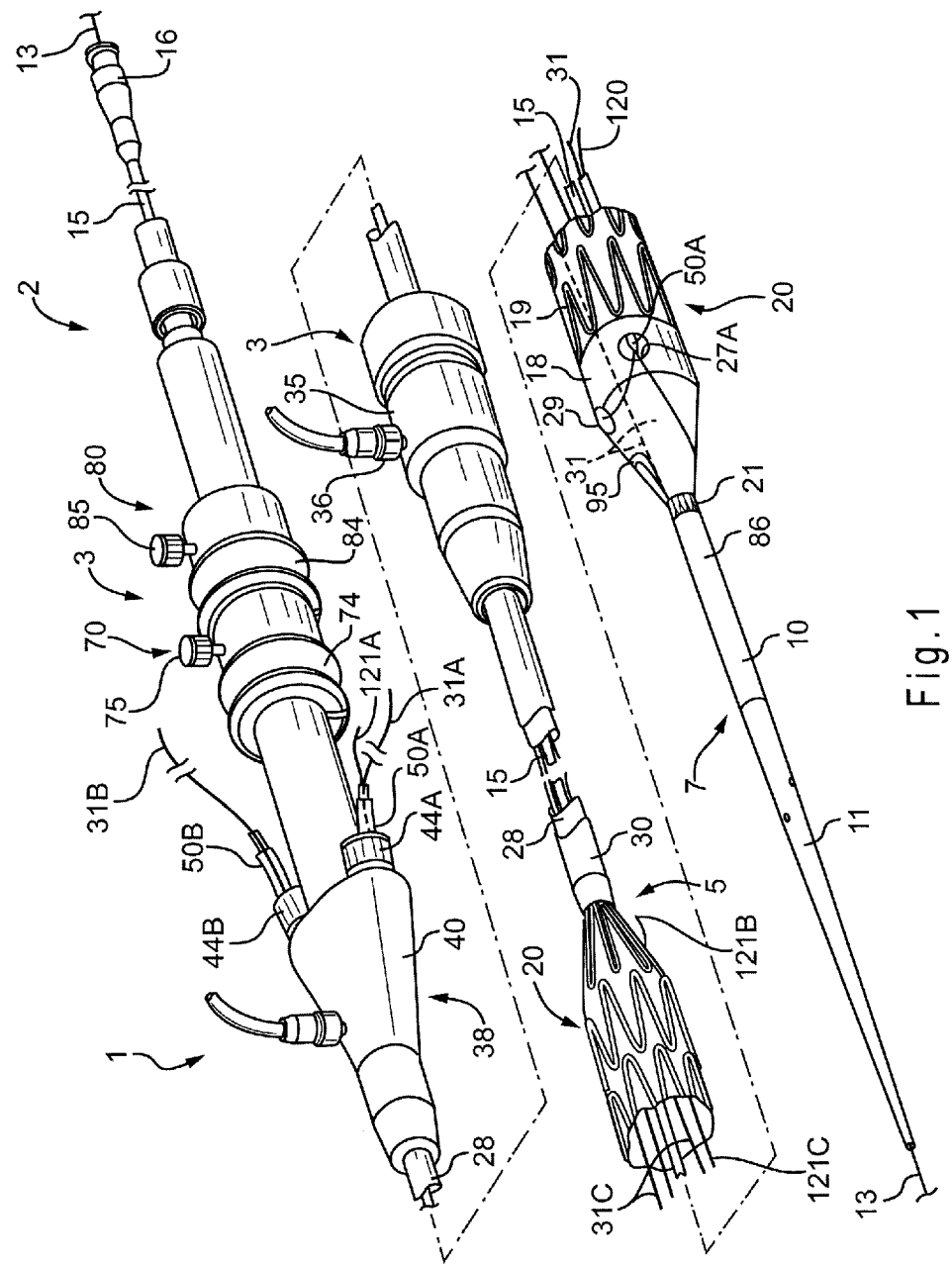
FIG. 1 depicts a system for delivering and deploying an endoluminal prosthesis with a precannulated fenestration.

FIG. 1 shows a system 2 for delivering and deploying an endoluminal prosthesis 20 with one or more precannulated fenestrations in a vessel of a patient. The system 2 includes a delivery catheter 1 comprising an external manipulation section 3, a distal positioning mechanism or attachment region 5, and a proximal positioning mechanism or attachment region 7. The distal and proximal attachment regions 5, 7 are positioned inside the patient's body during a medical procedure, whereas the external manipulation section 3 is positioned outside the patient's body. During a procedure, the operator controls or manipulates the external manipulation section 3 to position the distal and proximal regions 5, 7 and to release the prosthesis 20 into the vessel.

The delivery and deployment system 2 may also include the prosthesis 20 disposed at a proximal introduction end portion of the delivery catheter 1 between the distal and proximal attachment regions 5, 7. The prosthesis 20 may include a tubular body of graft material or tubular graft 18. The prosthesis 20 may additionally or alternatively comprise a support structure (shown as one or more expandable stents 19) coupled to the tubular graft 18 and disposed at least partly coextensive with the tubular graft 18. Each stent 19 may be coupled to an interior surface 23 and/or an exterior surface 24 (shown in FIG. 7B) of the tubular graft 18 of the prosthesis 20. The prosthesis 20 shown in FIG. 1, and other figures, includes the tubular graft 18 and the plurality of expandable stents 19 disposed coextensive with the tubular graft 18. In addition, the prosthesis 20 shown in FIG. 1 includes a proximal stent 21 extending from the distal outflow end of the tubular graft 18 so that it is at least partially uncovered from the tubular graft 18. The proximal stent 21 expands and engages the body lumen of the patient, thereby anchoring the prosthesis 20 and preventing the prosthesis from moving after implantation. The proximal stent 21 may include anchoring means, for example barbs (not shown) that are configured to grasp the walls of the body lumen of the patient.

The prosthesis 20 shown in FIG. 1 includes one or more fenestrations, as will be described below. Each of the fenestrations is disposed in a sidewall of the graft material between proximal inflow and distal outflow axial end openings of the tubular graft material. The fenestration provides a fluid pathway through the sidewall of the graft tube and allows the prosthesis to be placed in a main vessel in overlapping relationship with an intersecting branch vessel, without interrupting flow to the branch vessel. Each of the fenestrations may be used to permit the pass through of a secondary graft or connecting prosthesis having one end coupled to the prosthesis 20 through the corresponding fenestration, and the other end anchored into the walls of the branch vessel. Examples of systems for deploying a prosthesis with a fenestration and a proximal stent are disclosed in U.S. Pat. Nos. 9,101,455, 9,149,382, and in U.S. Patent Application Publication No. 2012/0041535, which are incorporated herein by reference in their entirety.

Prosthesis 20 is retained over the delivery catheter 1 by an outer sheath 30 that is movable between an extended delivery position and a retracted position. The outer sheath 30 includes an elongated tubular body defining an axial lumen 30A. The outer sheath 30 extends distally to the manipulation region 3. The prosthesis 20 is disposed within the axial lumen 30A of the outer sheath 30 in a radially compressed configuration during delivery. In FIG. 1, the prosthesis 20 is depicted in a partially deployed state, whereby the outer sheath 30 is partially retracted from the prosthesis 20, exposing the prosthesis and allowing it to radially expand to a radially expanded configuration. The outer sheath 30 may include a flexible structure that is able to bend and flex to negotiate complex and tortuous inner body lumina. The outer sheath 30 may be made of a biocompatible plastic such as PTFE, polyethylene, nylon, or the like. Examples of suitable sheath devices and materials are disclosed in U.S. Pat. Nos. 5,380,304, 6,589,227, and 7,025,758, and in U.S. Patent Application Publication Nos. 2001/0034514, 2002/0032408, and 2006/01555302, which are incorporated herein by reference in their entirety.

The delivery catheter shown in FIG. 1 further includes an inner cannula 15 that extends proximally from the external manipulation region 3 to the distal attachment region 7. The inner cannula 15 defines an axial lumen (not shown) that is configured to receive a guide wire 13. The inner cannula 15 extends proximally from a distal end portion of the delivery catheter 1 to a proximal end portion of the delivery catheter 1. A tapered extension 11 is fixedly coupled to the proximal end of the cannula 15 and forms the proximal introduction end 10 of the delivery catheter 1. A fluid port 16 is coupled to the distal end of the inner cannula 15. The fluid port 16 is adapted to accept a syringe and may be used to introduce reagents into the body lumen of the patient.

Inner cannula 15 is slidingly disposed within the lumen 30A of the outer sheath 30. The prosthesis 20 is retained over a distal portion of the inner cannula 15 by the outer sheath 30. The inner cannula 15 may be flexible so that the system 2 can be advanced within a relatively tortuous vessel, such as a femoral artery or the aortic arch. The inner cannula 15 may be made of metal, for example aluminum, stainless steel, or nitinol. The inner cannula 15 and the tapered extension 11 can form a mechanical coupling such that force exerted (rotating, pushing or pulling) to the inner cannula from the distal end can be transferred to the tapered extension 11 for axial movement. This allows the operator to control the tapered extension 11 remotely during a procedure. For example, the operator can rotate or slide the tapered extension 11 relative to the prosthesis 20 by manipulating the cannula 15.

The delivery catheter 1 shown in FIG. 1 further includes an elongated tubular pusher 28 that extends distally from the manipulation region 3 to the distal attachment region 5. The inner cannula 15 is slidably disposed within an axial lumen 33 (shown in FIGS. 2 and 6) defined by a tubular body of the pusher 28. The outer sheath 30 is slidably disposed over an end portion of the pusher 28. The pusher 28 may include any suitable biocompatible material including metal or plastic. The pusher 28 may include a radiopaque material. Suitable materials include, but are not limited to aluminum, nitinol, nylon, polypropylene, and polyethylene. The pusher 28 may have high longitudinal column strength to ensure adequate force transfer between the user and the prosthesis during deployment.

The delivery and deployment system 2 may include a hemostatic sealing unit 35 for controlling blood loss through the delivery and deployment system 2. The sealing unit 35 is fixedly connected to the outer sheath 30 and couples the sheath and the pusher 28. The sealing unit 35 includes one or more hemostatic valves (not shown) that provide a hemostatic seal between the outer sheath 30 and the pusher 28. Suitable hemostatic valves include, for example, disk valves, iris valves, and the like. The hemostatic sealing unit 35 may also include a side tube 36 that facilitates the introduction of medical reagents between the walls of the pusher 28 and the outer sheath 30. U.S. Pat. Nos. 6,416,499 and 7,651,519, and U.S. Patent Application Publication Nos. 2005/0171479 A1 and 2007/0078395 A1 describe examples of suitable hemostatic sealing devices that can be used with a delivery catheter described in the present application. Each of these patent references is incorporated by reference herein in its entirety.

The distal end of the pusher 28 is disposed adjacent the distal inflow end of the prosthesis 20. To deploy the prosthesis 20, the operator slides the outer sheath 30 distally while applying proximal pressure to the pusher 28 in the user manipulation region 3. The pusher 28 is configured to prevent the prosthesis 20 from sliding distally with the outer sheath 30 when the outer sheath 30 is distally withdrawn. As a result, the outer sheath 30 retracts distally from the prosthesis 20, exposing the prosthesis for radially outward expansion.

In FIG. 1, the distal end of the pusher 28 is connected to an auxiliary access device 38. With additional reference to FIG. 3, the access device 38 is shown including a housing 40, channels 42A, 42B extending generally axially through the housing 40, and ports 44A, 44B coupled to and in communication with the channel 42A, 42B, respectively. The ports 44A, 44B provide fluid and mechanical communication between the user manipulation section 3 and the channels 42A, 42B, respectively, which provides fluid and mechanical communication with the axial lumen 33 of the pusher 28 which, in turn, provides fluid and mechanical communication with the prosthesis 20. The ports 44A, 44B may be used, for example, to introduce medical reagents to the prosthesis 20 through the pusher 28. Alternatively or additionally, the ports 44A, 44B may be used to introduce auxiliary medical devices such as guide wires or interventional catheters to the prosthesis through the pusher 28. The access device 38 may include one or more hemostatic valves (not shown), as described above, to control blood loss during a procedure. For example, one or more ports 44A, 44B may include one or more disk valves, iris valves, or the like. Alternatively or additionally one or more such valves may be placed within one or both channels 42A, 42B to control blood loss through the access device 38.

Figure 4:
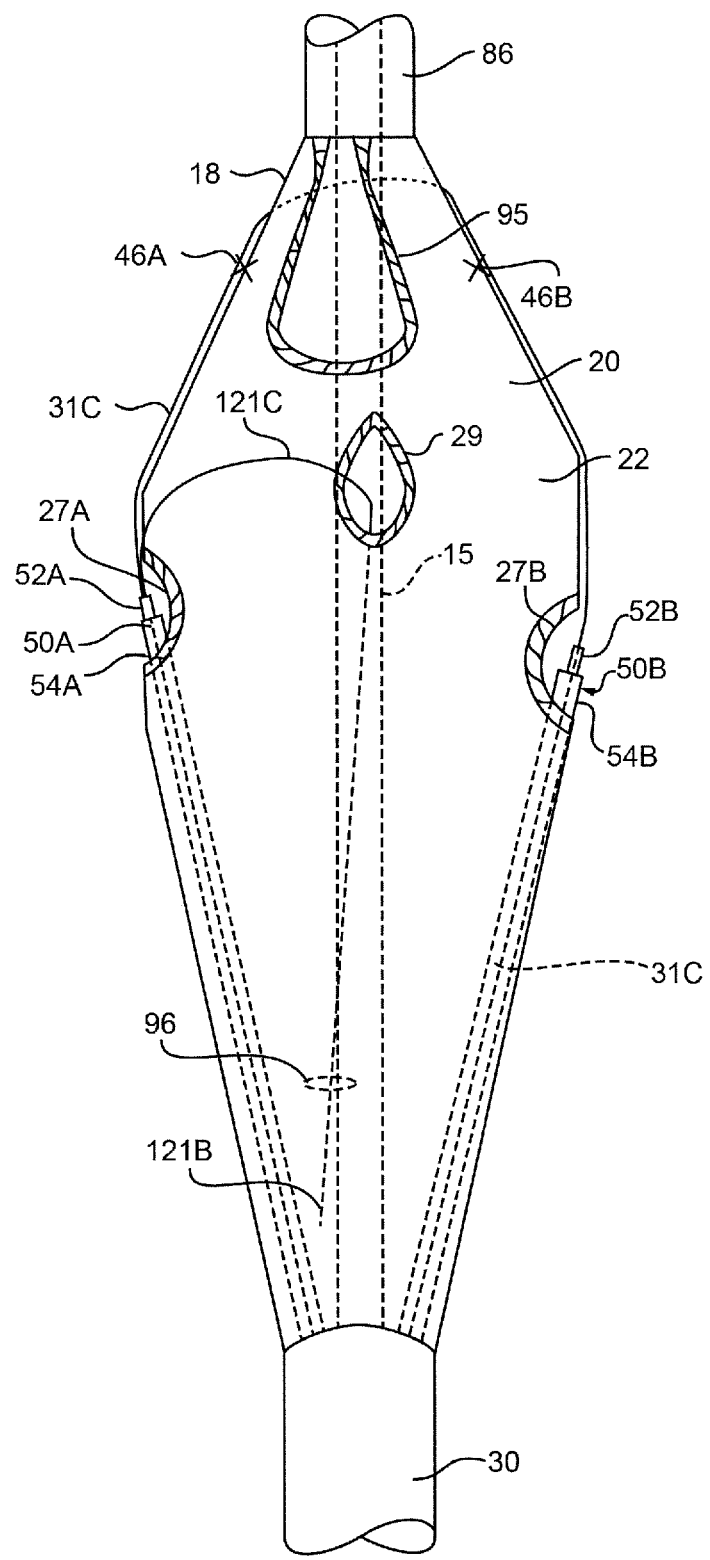
FIG. 4 depicts a proximal portion of a system for delivering and deploying a prosthesis, including a prosthesis with a precannulated fenestration.

An example of a delivery and deployment system 2 comprising the prosthesis 20, where the fenestrations may include a first lateral fenestration 27A, a second lateral fenestration 27B, and/or an anterior fenestration 29, as shown in FIGS. 1 and 4. The terms "first," "second," "third", and so forth may be used in front of the fenestrations or other elements are used merely for readable, and these terms can be used in front of either of the fenestrations and elements depending on the system. In an example, the prosthesis 20 may include one or both lateral fenestrations 27A, 27B, in addition to any one of the additional features described herein. At least one of the lateral fenestrations and the anterior fenestration is precannulated. To precannulate a first branch prosthesis, the system 2 can include a guide 31 having a first end 31A, a second end 31B, and a body portion 31C disposed between the ends. The guide 31 may be formed of a wire or a tubular body from any suitable material, such as a biocompatible metal or plastic, and with dimensions suitable for the particular application. In one example, a wire includes a highly elastic metal, such as nitinol or the like, and has a diameter in the range of about 0.016 to about 0.018 inches. Wires and tubular bodies made of other materials, and having other diameters are also contemplated.

Figure 6:
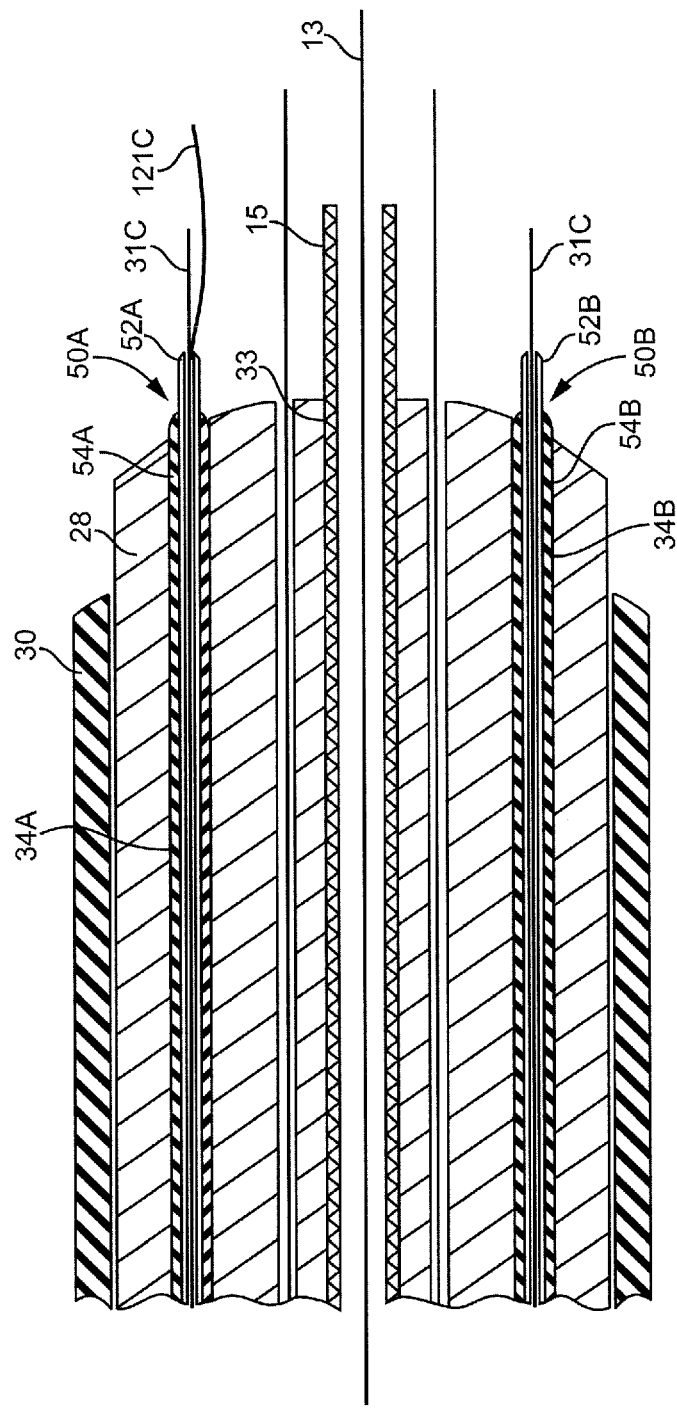
FIG. 6 is a cross-sectional view of a proximal portion of a pusher of a system for delivering and deploying a prosthesis with a precannulated fenestration, comprising auxiliary catheters and a precannulating wire structure.

The guide 31 traverses the delivery catheter 1 between proximal and distal end portions of the catheter 1. Each wire end 31A, 31B is disposed at the external manipulation section 3 of the delivery catheter 1 and can be directly manipulated by the operator during a procedure. The guide 31 extends proximally from the first end 31A through port 44A, through the axial lumen 33 (shown, for example, in FIG. 3) of the pusher 28, into a lumen 32 of the prosthesis 20 (shown, for example, in FIG. 4), and through lateral fenestrations 27A, 27B along the exterior surface 24 of the tubular graft 18 (shown, for example, in FIGS. 1 and 3). The guide 31 then extends proximally through the lumen 32 of the prosthesis 20, through the axial lumen 33 (shown, for example, in FIG. 3), and out through port 44B towards the second wire end 31B. In some examples, the axial lumen may include a single lumen structure and the guide 31 will extend proximally and distally along the delivery catheter through a single lumen structure. In other examples, the axial lumen may include a multi-lumen structure and the guide 31 will extend proximally and distally along the delivery catheter through separate lumen structures. On example of such multi-lumen structure is shown in FIG. 6. Here, the pusher 28 includes its axial lumen 33 centrally located, and one or more secondary lumens 34A or 34B extending within the wall of the pusher 28 and generally align with the more centrally located axial lumen 33. The secondary lumens 34A, 34B can receive sheath systems 50A and 50B, respectively, and/or the first guide body 31C and the second guide body 121C, as shown.

The guide 31 is slidably disposed within the lateral fenestrations 27A, 27B. Consequently, the operator can move the guide 31 proximally through the lateral fenestrations 27A, 27B by pulling distally on the first wire end 31A or by pushing distally on the second wire end 31B, or vice versa. This feature provides the operator with control over the positioning and configuration of the guide 31 with respect to the lateral fenestrations 27A, 27B. For example, it may be possible to manipulate the angle of the guide 31 as it passes through the lateral fenestrations 27A, 27B by fixing the position of the first wire end 31A and manipulating the second wire end 31B, or vice versa. Other advantages of this feature will be apparent to one of ordinary skill in the art.

FIG. 4 depicts an example of the prosthesis 20 with multiple (more than one) precannulated lateral fenestrations 27A, 27B. One or more stabilizing sutures 46A, 46B may be provided along the prosthesis 20 to attach the body portion 31C of the guide 31 to the tubular graft 18 and/or to the stent 19. Sutures 46A, 46B preferably limit lateral movement of the body portion 31C, but allow the guide 31 to slide axially through the lateral fenestrations 27A, 27B, as described above. The guide 31 may pass through the lumen 32 of the prosthesis 20 as it traverses the lateral fenestrations 27A, 27B. In some examples, the body portion 31C of the guide 31 extends approximately 3 cm or more away from the lateral fenestration 27A, 27B and then passes through the tubular graft 18 into the lumen 32 of the prosthesis 20. In other examples, the guide extends approximately 6 cm or less away from a fenestration and then passes through the tubular graft into the lumen 32 of the prosthesis. In other examples, the guide 31 traverses lateral fenestrations 27A, 27B without passing through the lumen 32 of the prosthesis 20.

Figure 3:
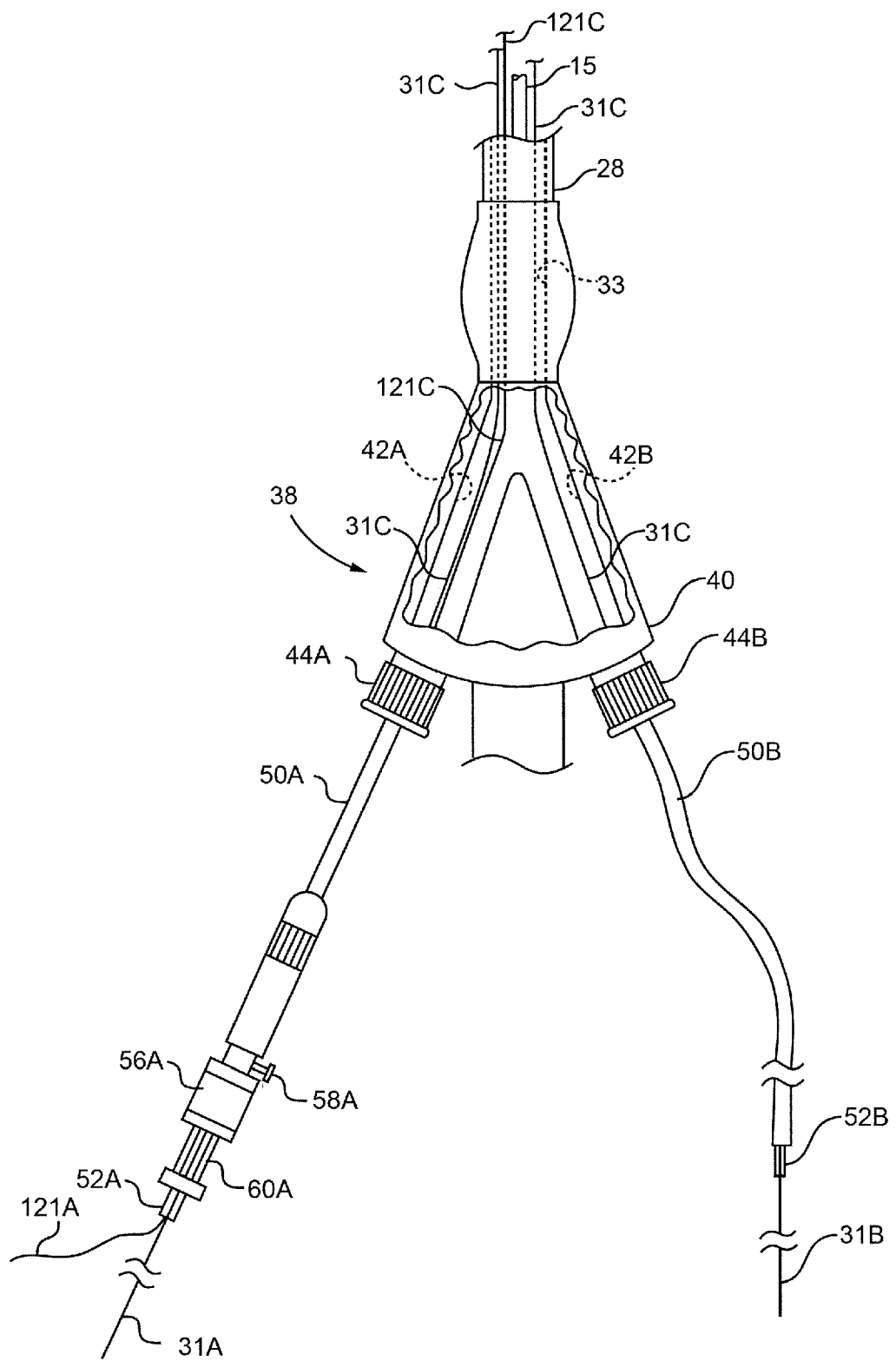
FIG. 3 depicts a distal portion of a system for delivering and deploying a prosthesis with a precannulated fenestration.

As shown in FIGS. 1, 3, and 4, sheath systems 50A, 50B may be provided and delivered to or preloaded within the prosthesis 20 through the auxiliary access device 38. The sheath systems 50A, 50B may include, for example, an elongated tubular sheath 54A, 54B and an elongated dilator 52A, 52B, respectively, slidably disposed within an axial lumen of the respective sheaths 54A, 54B. The sheath systems 50A, 50B may also include hemostatic sealing unit, as described above, to limit or prevent blood loss through the auxiliary catheters, although while both may include them, FIG. 3 depicts only sheath system 50A including a hemostatic sealing unit 56A. In addition, the sheath systems 50A, 50B may include side tubes, again only sheath system 50A is depicted including a side tube 58A for introducing medical reagents through the auxiliary catheters. The dilators 52A, 52B terminate distally at connection means configured for introducing medical reagents through the auxiliary catheters. 60A, 60B. For example, the dilator 52A is depicted including such connection means 60A.

The sheath systems 50A, 50B are can be delivered to the prosthesis 20 over the respective wire ends 31A, 31B through the axial lumen 33 or lumens 34A or 34B of the pusher 28, as described above. The auxiliary catheters may be used to deliver medical devices, such as guide wires, balloons, stents, stent grafts, imaging devices, and the like, from the user manipulation section 3 to the prosthesis 20. For example, as described in greater detail below, the sheath systems 50A, 50B may be used to cannulate target branch vessels through the lateral fenestrations 27A, 27B.

Figure 2:
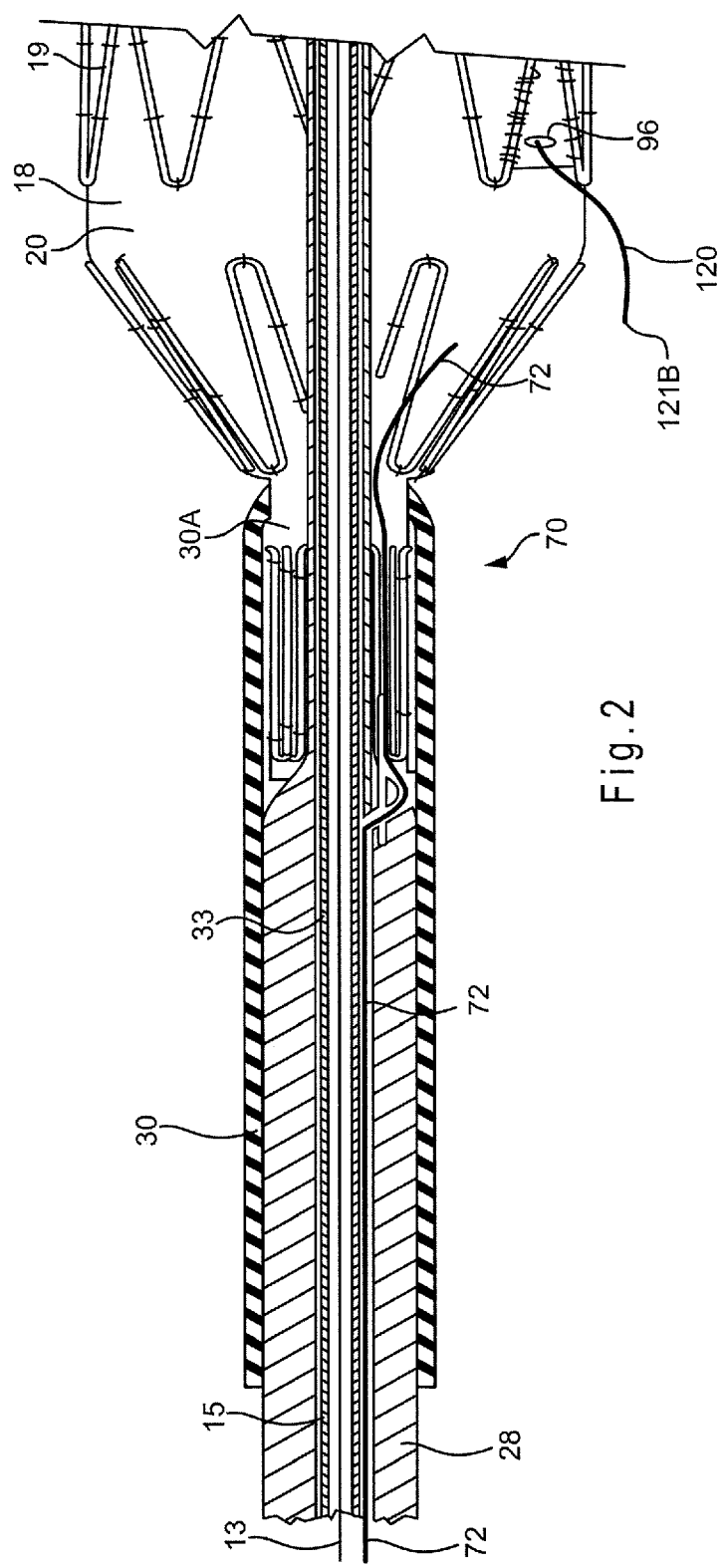
FIG. 2 is a cross-sectional view of a distal attachment region of a system for delivering and deploying an endoluminal prosthesis with a precannulated fenestration.
Figure 5:
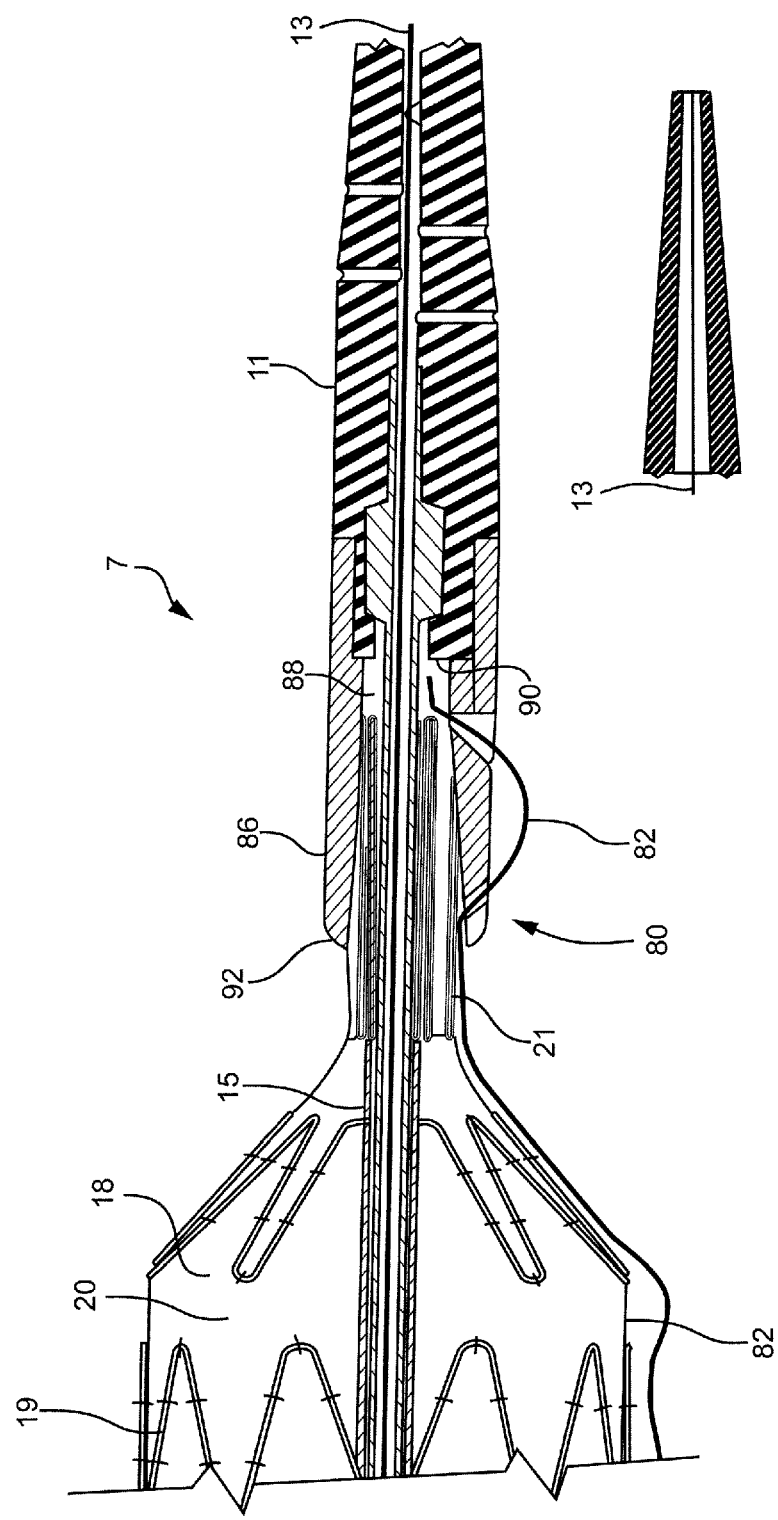
FIG. 5 is a cross-sectional view of a proximal attachment region of a system for delivering and deploying a prosthesis with a precannulated fenestration.

As shown in FIGS. 1, 2, and 5, one example of the system 2 for delivering and deploying a prosthesis may optionally include one or more retention devices for retaining at least a portion of the prosthesis. For example, the delivery catheter 1 may include a distal prosthesis retention device 70 for retaining a distal inflow end of the prosthesis 20, and a proximal prosthesis retention device 80 for retaining a proximal outflow end of the prosthesis 20. FIGS. 1 and 2 depict an example of the distal prosthesis retention device 70 including a distal trigger wire 72. The trigger wire 72 can be extended between the prosthesis 20 and the external manipulation section 3 through the axial lumen 33 of the pusher 28. The trigger wire 72 is preferably disposed in a lumen separate from the guide 31 for cannulation to prevent entanglement between the wires. A distal end of the trigger wire 72 is connected to control member 74 (FIG. 1). A proximal end of the trigger wire 72 is removably connected to the distal inflow end of the prosthesis 20 (FIG. 2) and limits axial displacement of the prosthesis 20. The trigger wire 72 can be disconnected from the distal end of the prosthesis 20 by manipulating the control member 74, for example by sliding the control member 74 distally to pull the wire away from the prosthesis 20. A clamping screw 75 may be provided to clamp the control member 74 to prevent inadvertent disengagement of the trigger wire 72.

Figure 9:
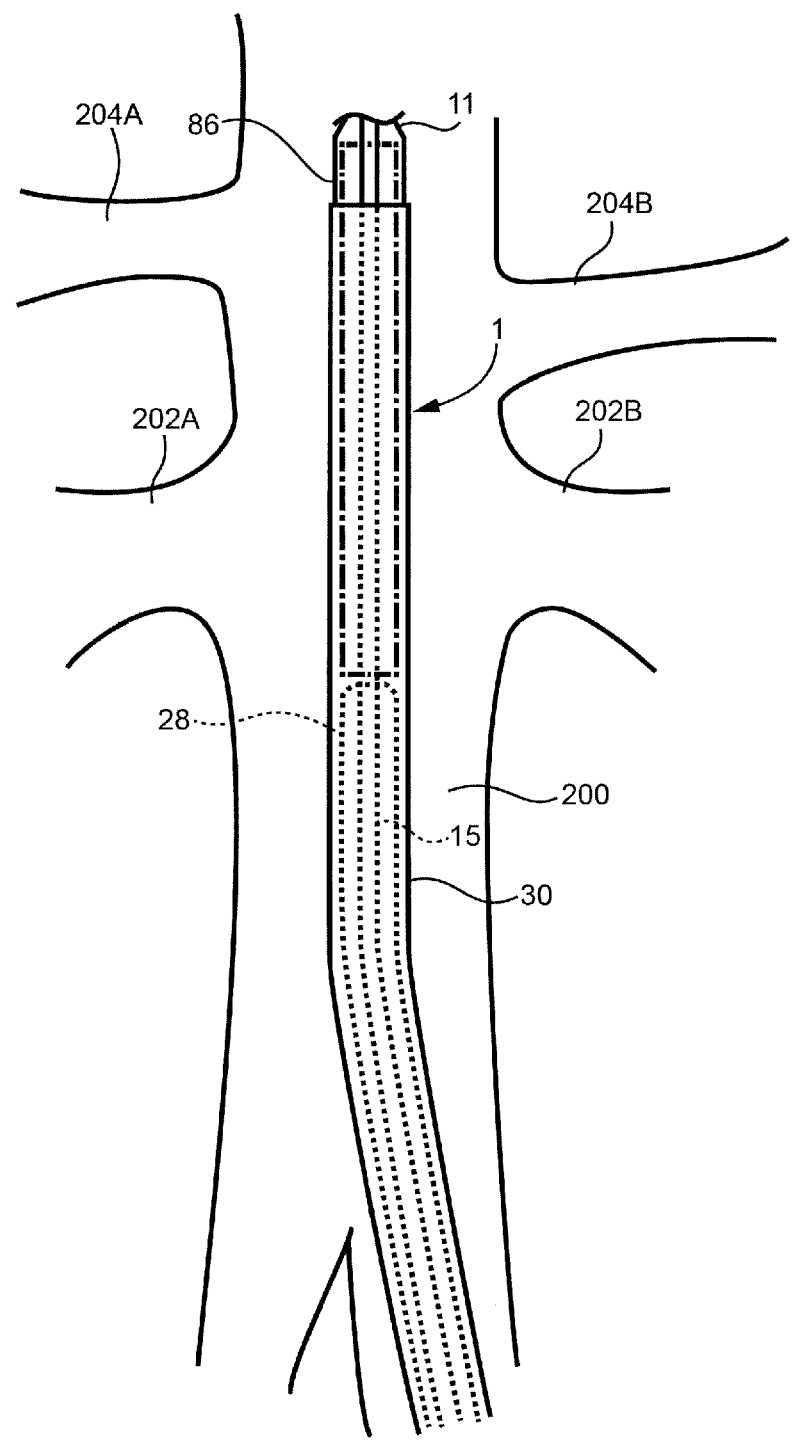
FIGS. 9-15 depict various stages of a method of using a delivery and deployment system including a prosthesis with precannulated fenestrations.

FIGS. 1 and 5 depict an exemplary proximal prosthesis retention device 80 comprising a proximal trigger wire 82 and a proximal top cap 86. The top cap 86 is fixedly coupled to the tapered extension 11. The top cap 86 can have a tubular body to defining a cap lumen 88 extending from the substantially closed distal end 90 of the tapered extension 11 to a distal end opening 92 to receive and hold the proximal outflow end of the prosthesis 20 in the radially compressed configuration. In one example, a portion of the lumen 30A the outer sheath 30 and the cap lumen 88 of the top cap 86 together define a delivery lumen 89 to maintain the prosthesis 20 in the radially compressed configuration, as shown in FIG. 9. The top cap 86 may include any suitable biocompatible material including metal or plastic. The top cap 86 may include a radiopaque material. Suitable materials include, but are not limited to aluminum, nitinol, nylon, polypropylene, and polyethylene. The top cap 86 may prevent the proximal outflow end of the prosthesis 20 from expanding during use. The proximal trigger wire 82 can be extended between the prosthesis 20 and the external manipulation section 3 through the axial lumen 33 of the pusher 28. The proximal trigger wire 82 is preferably disposed in a lumen separate from the cannulating guide 31 to prevent entanglement of the wires. A distal end of the proximal trigger wire 82 is connected to a control member 84 (FIG. 1). A proximal end of the wire 82 is removably connected to the proximal outflow end of the prosthesis 20 and to the top cap 86. The proximal trigger wire 82 can be disconnected from the prosthesis 20 and the top cap 86 by manipulating the control member 84, for example by sliding the control member distally to pull the wire away from the prosthesis and the top cap. A clamping screw 85 may be provided to clamp the control member 84 to prevent inadvertent disengagement of the trigger wire 82. Once the wire 82 disengages the prosthesis 20 and the top cap 86, the top cap 86 can be removed from the prosthesis 20 by sliding the inner cannula 15, the tapered extension 11, and the top cap 86, each coupled together, proximally with respect to the pusher 28.

Various devices and systems for retaining proximal, distal, and medial portions of a prosthesis are disclosed in the patent literature, for example U.S. Pat. Nos. 6,524,335, 7,335,224, 7,435,253, 7,537,606, 7,611,529, 7,651,519, and 7,722,657, and U.S. Published Patent Application Nos. 2004/230287 A1, 2006/0004433 A1, 2007/0043425 A1, and 2008/0294234 A1 disclose devices and systems that are suitable for use with the present invention. Each of these patent references is incorporated herein by reference in its entirety.

Figure 7A:
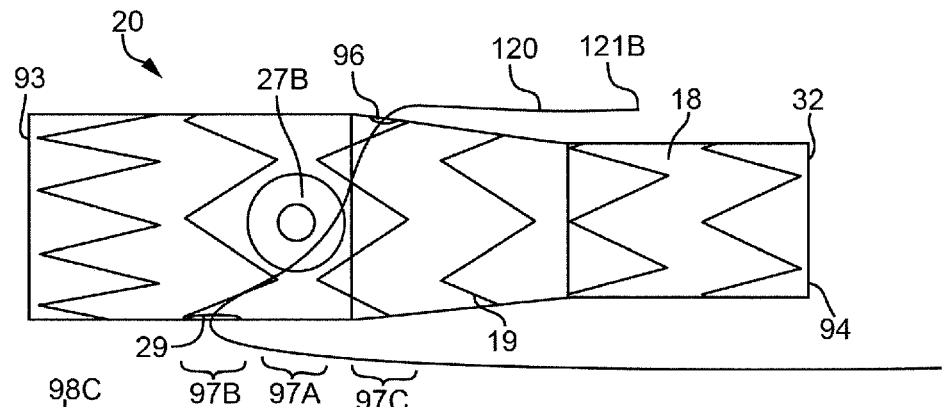
FIG. 7A is a plan view of a prosthesis and a precannulating wire structure extending between a fenestration and an opening.
Figure 7B:
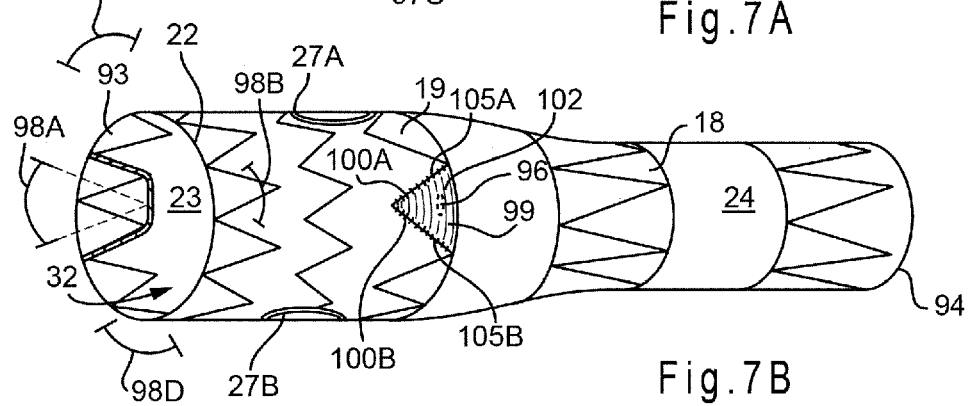
FIG. 7B is a perspective view of an exemplary prosthesis with an anterior opening and a patch.

FIGS. 7A-7B depicts an example of the prosthesis 20 in its radially expanded configuration that would be reduced to its radially compressed configuration and loaded into the system 2. The tubular graft 18 defines a first or proximal outflow axial end opening 93, a second or distal inflow axial end opening 94, and the lumen 32 extending longitudinally there through. The lateral fenestrations 27A, 27B (hereinafter the first lateral fenestration 27A and the second lateral fenestration 27B) are formed in a sidewall 22 of the tubular graft 18. The positions of the first lateral fenestration 27A and the second lateral fenestration 27B can be disposed along a third axial segment 97A of the tubular graft 18. Generally, the first lateral fenestration 27A and the second lateral fenestration 27B can be spaced from one another circumferentially about the tubular graft to face different lateral directions depending on the locations of the branch vessels of the patient. In the non-limiting example of FIGS. 7A-7B, the first and second lateral fenestrations 27A and 27B are disposed in the tubular graft 18 at locations between about 90 and about 270 degrees apart, though the positioning may be greater or less. In one example, the lateral fenestrations 27A, 27B are on opposite sides of the tubular graft material, and in some cases, about 180 degrees from one another.

The anterior fenestration 29 can be formed in the sidewall 22 of the tubular graft 18. The anterior fenestration 29 can be disposed along a first axial segment 97B of the tubular graft 18 below the first end opening 93. The first axial segment 97B may be proximal to the third axial segment 97A or closer to the first end opening 93 than the third axial segment 97A such that the third axial segment 97A is below the first axial segment 97B. In one example, the axial segments 97A, 97B may overlap. Generally, the anterior fenestration 29 can be disposed circumferentially about the tubular graft generally in the anterior direction to face a different direction than at least one of the first and second lateral fenestrations 27A, 27B depending on the location of the third branch vessel of the patient. In one example, the anterior fenestration 29 can be positioned at about 75 to about 115 degrees (preferably about 90 degrees) from at least one of the first and second lateral fenestrations 27A, 27B.

As shown in FIG. 4, a scalloped opening 95 can be formed in the sidewall 22 of the tubular graft 18. The scalloped opening 95 can be disposed along an axial segment of the tubular graft 18 proximate to the first end opening 93 and the proximal stent 21. Generally, the scalloped opening 95 can be disposed circumferentially about the tubular graft 18 to face a different direction, generally the posterior direction, than at least one of the first and second lateral fenestrations 27A, 27B depending on the location of the fourth branch vessel of the patient. In one example, the scalloped opening 95 can be positioned at about 75 to about 115 degrees (preferably about 90 degrees) from at least one of the first and second lateral fenestrations 27A, 27B. In one example, the scalloped opening 95 and the anterior fenestration 29 face generally the same direction.

A posterior opening 96 can be formed in the sidewall 22 of the tubular graft 18. The posterior opening 96 can be disposed along a second, axial segment 97C of the tubular graft 18 below the lateral fenestrations 27A, 27B. The second axial segment 97C being distal to the first axial segment 97B or closer to the second end opening 94 than the first axial segment 97B, and in some instances, closer than the third axial segment 97A. In one example, the second and third axial segments 97C, 97A may overlap. Generally, the posterior opening 96 can be disposed circumferentially about the tubular graft to face a different direction, generally the posterior direction, than at least one of the first and second lateral fenestrations 27A, 27B. In one example, the posterior opening 96 can be positioned at about 75 to about 115 degrees (preferably about 90 degrees) from at least one of the first and second lateral fenestrations 27A, 27B.

Generally, the terms "anterior" and "posterior" when referring to the prosthesis refers to different circumferential regions along the prosthesis surface that are opposite facing relative to the lateral facing ones. A circumferential region can be defined as a portion (generally less than, for example, about +/−15 degrees from a centerline of the opening or fenestration included within the portion) of the entire circumference (360 degrees) of the prosthesis from an axial sectional view of the prosthesis. For example, the posterior opening 96 is disposed along a different circumferential region than the anterior fenestration 29. In one example, the centerline associated with a second circumferential region 98B (or posterior region) where the posterior opening 96 is located is disposed about +/−90 degrees to about 180 degrees from the centerline associated with a first circumferential region 98A (or anterior region) where the anterior fenestration 29 is located. In one example, the first lateral fenestration 27A is disposed in a third circumferential region 98C (or a first lateral direction disposed between the anterior and posterior regions), and the second lateral fenestration 27B is disposed along a fourth circumferential region 98D (or a second lateral direction, different than the first lateral direction, disposed between the anterior and posterior regions)) that is different than the third circumferential region 98C. The centerlines associated with the first, second, third, and fourth circumferential regions 98A, 98B, 98C, 98D can be spaced from one another by about 90 degrees (+/−15 degrees). In one example, the posterior opening is sized to allow the passage of a device, such as, e.g., a guide wire and a catheter for cannulation of a body lumen of a patient.

To inhibit leakage of body fluid, such as endoleak, through the posterior opening 96, a patch 99 can be coupled to the tubular graft 18 of the prosthesis 20 to cover at least partially the posterior opening 96. The patch 99 can be coupled to an outer and/or inner portion of the tubular graft 18. In one example, the patch is coupled to an outer portion of the graft material. The patch 99 can be coupled to the tubular graft in such a way to cover the posterior opening 96 and yet still allow the passage of devices through the posterior opening 96. In one example, one or more sides of the patch 99 surrounding the posterior opening 96 are coupled to the tubular graft (shown as coupled sides 100A, 100B), and at least one side (shown in FIG. 7B as the side facing the second end opening of the prosthesis), remains uncoupled to the tubular graft (shown as an uncoupled side 102) to allow the passage of devices from along the exterior surface 24 of the prosthesis 20 to within the lumen 32 of the prosthesis 20. There can be one side of the patch coupled, as well as there can be multiple sides of the patch uncoupled. The shape of patch 99 is shown as triangular, but it can be other shapes such as rectangular and oval. The material of the patch 99 can be a graft material, as listed below, and can encourage a bio-seal between the graft materials of the prosthesis 20 and the patch 99, preferable after the procedure.

In one example, the posterior opening 96 can be located within a region defined by a pair of stent members 105A, 105B of one of the expandable stents 19 that are coupled to one another to form an angle there between. This can be formed inside of the apex of stent members in one or two stent members below the fenestrations 27A, 27B. The stent members 105A, 105B can provide a support around the posterior opening during the passage of the devices. In one example, the patch 99 is coupled to the tubular graft 18 and the stent members 105A, 105B. The patch may be placed between the stent members and the tubular graft so as to be in close proximity to the tubular graft for the bio-seal. In one example, as shown, the patch 99 forms a triangular patch having two of its sides 100A, 100B coupled along the stent members 105A, 105B, while leaving the third side the uncoupled side 102.

Figure 8A:
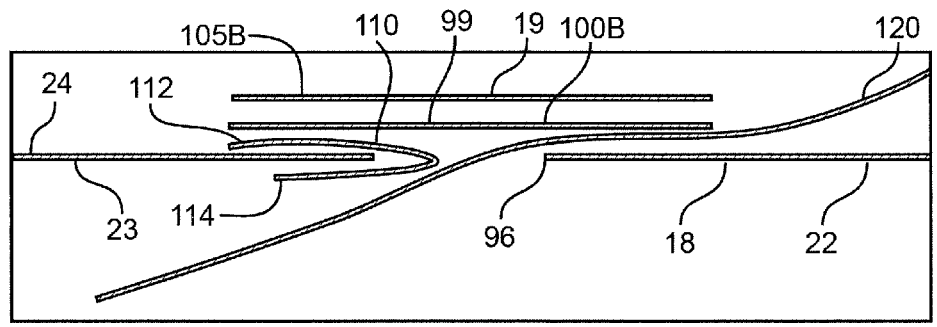
FIGS. 8A-8B are cross-sectional details of an exemplary prosthesis at an anterior opening, depicting a patch and a flap that is movable between open and closed positions.
Figure 8B:
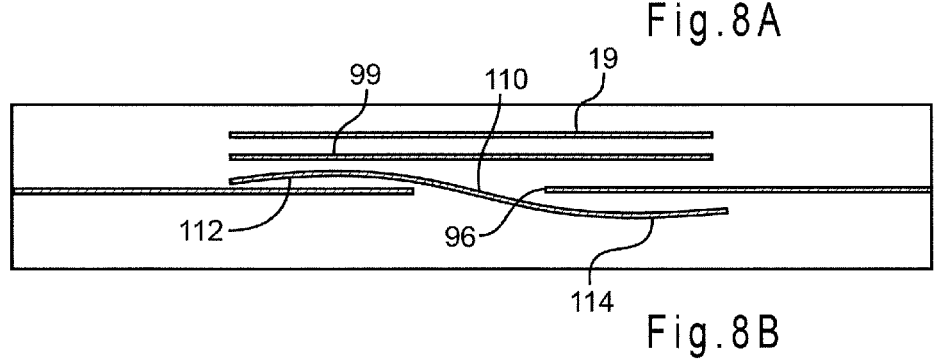

In one example, shown in FIGS. 8A-8B, the patch 99 can take the form of a flap patch or a flap patch 110 can be used in addition to the patch 99. The flap patch 110 can include an outer segment 112 disposed along an outer portion of the tubular graft 18 and an inner segment 114 extending through the posterior opening 96. The inner segment 114 is movable between an open position (FIG. 8A) to allow communication through the posterior opening 96, and a closed position (FIG. 8B) to inhibit communication through the posterior opening 96. The inner segment 114 can be tied to a separate trigger wire extending through the pusher lumen that can be pushed or pulled externally to move the inner segment 114 between its open and closed positions. Fluid pressure from within the lumen 32 of the prosthesis 20 can then facilitate closure of the inner segment 114 and the inner and outer segments can form a bio-seal with the tubular graft 18. The flap patch 110 can be made of graft material, as described below, and include a super-elastic material frame or portion, which include a shape-memory alloy, such as a nickel titanium alloy (nitinol). To this end, closure of the flap patch 110 can be automatically activated by the temperature set of the shape-memory alloy.

In one example, an endoluminal prosthesis includes a tubular graft body and a support structure coupled to the tubular graft body, a first end opening, a second end opening, and a lumen extending longitudinally therethrough between the first and second end openings. An anterior fenestration is defined in a sidewall of the tubular graft body along a first axial segment and along a first circumferential region of the prosthesis. An opening defined in the sidewall along a second axial segment and a second circumferential region of the prosthesis. The second axial segment is closer in proximity to the second end opening than the first axial segment. The second circumferential region is different than the first circumferential region, for example, such as about 90 degrees to about 180 degrees from the first circumferential region. A lateral fenestration is defined in the sidewall along a third axial segment of the tubular body. The third axial segment is disposed between the first and second axial segments. A patch may be coupled to the tubular graft body, and disposed to cover the opening. The patch may be disposed in a region defined by the pair of stent members of the support structure angled toward one another. An outer segment of a flap may be disposed along an exterior surface of the tubular graft body and an inner segment of the flap may extend through the opening. The inner segment is movable between an open position to allow communication through the opening, and a closed position to inhibit communication through the opening.

FIGS. 9-14 depict various stages of a method for delivering and deploying a prosthesis comprising one or more precannulated fenestrations into the aorta. Although the method is described in relation to a system for treating the aorta, it can readily be applied to other systems and indications.

The system 2 is provided with the delivery catheter 1, as described for example with respect to FIG. 1, the pusher 28 and the inner cannula 15 slidingly disposed within the axial lumen 33 of the pusher 28. The delivery catheter 1 is slidingly disposed within an axial lumen 30A of the outer sheath 30. The prosthesis 20 is disposed over the proximal end portion of the delivery catheter 1 within the axial lumen 30A of the outer sheath 30. The top cap 86 retains a proximal end portion of the prosthesis 20 to prevent premature radial expansion of the proximal end of the prosthesis 20 as the outer sheath 30 is retracted distally over the delivery catheter 1. Although not shown in FIGS. 9-14, the prosthesis 20 may include one or more expandable stents and the proximal stent 21, as described above.

FIG. 9 depicts the delivery and deployment system 2 disposed in a delivery configuration within a vessel 200 (such as the aorta). The system 2 includes the prosthesis 20 with multiple fenestrations 27A, 27B, 29 and the scalloped opening 95 sized and configured to provide fluid communication between the lumen 32 of the prosthesis 20 and the branch vessels 202A, 202B (such as renal arteries) and branch vessels 204A, 204B (such as the celiac and SMA arteries) after the prosthesis is deployed. Consequently, the prosthesis 20 can be placed within the vessel 200 so that the prosthesis overlaps the branch vessels 202A, 202B, 204A, 204B without occluding the branch vessels. The prosthesis 20 can include one or more precannulated lateral fenestrations 27A, 27B, as described above, and the precannulated anterior fenestration 29. In particular, the guide 31 is provided having its first end 31A, second end 31B, and wire body 31C. The guide 31 extends proximally from the first wire end 31A through the axial lumen of the pusher 28, into the lumen 32 of the prosthesis 20, and through the lateral fenestration 27A, traversing along the exterior surface 24 of the tubular graft 18. The guide 31 extends proximally from the exterior surface 24 of the tubular graft 18 through the lateral fenestration 27B into the lumen 32 of the prosthesis 20, and through the axial lumen of the pusher 28, as described herein, towards the second wire end 31B.

With reference to FIGS. 1-4, to precannulate another branch prosthesis, the system 2 includes another guide 120 having a first wire end 121A, a second wire end 121B, and a body portion 121C disposed between the ends. The second guide 120 may be a wire or a tubular body sized, shaped, and formed from any suitable material listed above with respect to the guide 31. The term "second" in front of the guide 120 is used merely for readable, and the term "second" can be used in front of the guide 31 and the term "first" can be used in front of the guide 120 depending on the system. The second guide 120 traverses the delivery catheter 1 between proximal and distal end portions of the catheter 1. The first wire end 121A can be disposed at the external manipulation section 3 of the delivery catheter 1 and directly manipulated by the operator during a procedure. The second guide 120 extends proximally from the first wire end 121A through port 44A, through one of the lumens (shown, for example, in FIG. 6) of the pusher 28, into the lumen 32 of the prosthesis 20 (shown, for example, in FIG. 4), and out through the lateral fenestration 27A, traversing along the exterior surface 24 of the tubular graft 18 and in through the anterior fenestration 29 (shown, for example, in FIGS. 4 and 7A). The second guide 120 then extends proximally within the lumen 32 of the prosthesis 20 traversing along the interior surface 23 of the prosthesis, and proximally out through the posterior opening 96. When the system is in the delivery position, the second wire end 121B of the second guide 120 is disposed at a location such that when the outer sheath 30 is withdrawn partially the second wire end 121B is free along the exterior surface 24 of the prosthesis 20. In one example, the second wire end 121B is axially located between the posterior opening 96 and the second axial end opening 94 of the prosthesis 20. In one example, the second wire end 121B extends from the posterior opening 96, along the underneath side of the patch 99 between the patch and the exterior surface 24 of prosthesis, and out from the uncoupled side 102 toward the second axial end opening 94. In one example, the sheath system 50A is positioned within (or delivered within) the prosthesis 20 over the first wire end 121A and body 121C of the second guide 120. The body 121C of the second guide 120 can be extended through the lumen of the sheath system 50A, which is shown extending through a lumen in the wall of the pusher 28, as shown in FIG. 6. In this manner, the second guide 120 and the guide 31 can both extend from the proximal tip of the sheath system 50A. The second guide 120 and the guide 31 can be disposed in the same lumen or in separate lumens defined in the dilator 52A and/or the sheath 54A or the pusher 28.

The second guide 120 is slidably disposed within the lateral fenestration 27A and the anterior fenestration 29. Consequently, the operator can move the second guide 120 distally through the lateral fenestration 27A and the anterior fenestration 29 by pulling distally on the first wire end 121A or by pushing proximally on the second wire end 121B using a snare device. Similarly, the operator can move the second guide 120 proximally through the lateral fenestration 27A and the anterior fenestration 29 by pushing proximally on the first wire end 121A or by pulling distally on the second wire end 121B after being coupled or attached to a snare device, as will be further described. This feature provides the operator with control over the positioning and configuration of the second guide 120 with respect to the lateral and anterior fenestrations 27A, 29. For example, it may be possible to manipulate the angle of the second guide 120 as it passes through the lateral and anterior fenestrations 27A, 29 by fixing the position of the first wire end 121A and manipulating the second wire end 121B, or vice versa. Other advantages of this feature will be apparent to one of ordinary skill in the art.

Returning to FIG. 9, the delivery catheter 1 may be delivered within the vessel 200 in a conventional manner. A guide wire (not shown) is introduced, for example, into one of the femoral arteries, through the corresponding iliac artery, and advanced into the vessel to the treatment location until the tip of the guide wire extends beyond the region in which the prosthesis 20 will be placed. The delivery and deployment system 2 is then inserted over the guide wire 13, via the lumen of the inner cannula 15, into the vessel 200 and positioned by radiographic techniques generally known in the art. Provisions may be made for a separate angiographic catheter (not shown) at the level of the branch vessels 202A, 202B, 204A, 204B.

Figure 10:
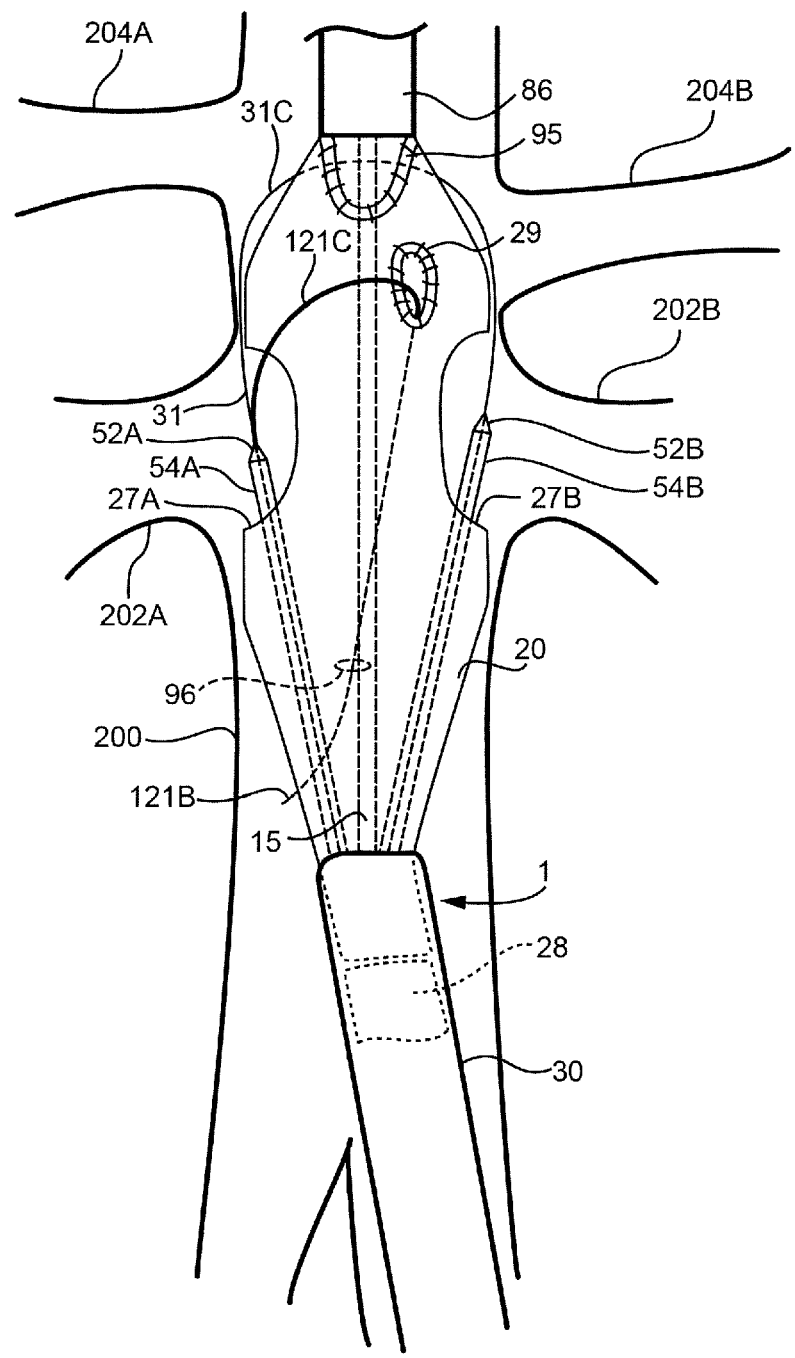

At this stage, the prosthesis 20 is disposed in its radially compressed configuration within the top cap 86 and the axial lumen 30A of the outer sheath 30. To this end, the delivery lumen 89 can maintain the prosthesis 20 in the radially compressed configuration, and contain the guide 31 and the second guide 120, and the sheath systems 50A, 50B within the prosthesis lumen. The sheath system 50A may be provided and inserted over the first wire end 31A of the guide 31 and the first wire end 121A of the second guide 120 and through port 44A into one of the axial lumens of the pusher 28 contained in the lumen of the delivery catheter 1. Likewise, the sheath system 50B may be provided and inserted over the second wire end 31B and through port 44B into the same or another axial lumen of the pusher 28. The delivery and deployment system 2 may be positioned within the vessel by radiographic means so that the prosthesis 20 overlaps the ostia of, and the lateral fenestrations 27A, 27B align with, the branch vessels 202A, 202B and the ostia, and the anterior fenestration 29 and the scalloped opening 95 align with, the branch vessels 204A, 204B. In one example, the delivery and deployment system 2 may be positioned within the vessel by radiographic means so that the anterior fenestration 29 of the prosthesis 20 aligns with the branch vessel 204B first for cannulation, and subsequently the lateral fenestrations 27A, 27B are aligned with the branch vessels 202A, 202B and the scalloped opening 95 is aligned the branch vessel 204A for subsequent cannulations. Once the catheter 1 is in a proper position, the outer sheath 30 is retracted to expose at least a portion of the prosthesis 20, or in some instances all of the prosthesis. The retraction of the outer sheath 30 can be made while maintaining the pusher 28 and the top cap 86 relatively in a fixed position. This action releases at least an intermediate portion including at least one of the anterior fenestration 29, the lateral fenestrations 27A, 27B, and the posterior opening 96 of the prosthesis 20 to expand radially to its radially expanded configuration towards the vessel walls, as shown in FIG. 10. The top cap 86 retains the proximal outflow end of the prosthesis 20, however, in its radially compressed configuration and prevents it from expanding at this stage. The operator may release the proximal outflow end of the prosthesis 20 at a desired stage by sliding the top cap 86 proximally with respect to the prosthesis.

The sheath system 50A may be advanced proximally over the guide 31 within the lumen 32 of the prosthesis 20 until the proximal end of sheath 54A passes through fenestration 27A. Similarly, the sheath system 50B may be advanced proximally over the guide 31 within the lumen 32 of the prosthesis 20 until the proximal end of sheath 54B passes through fenestration 27B. In one example, the sheath system 50A and/or the sheath system 50B can be preloaded within the delivery catheter 1 to save time for the procedure. In the preloaded configuration, the sheath systems can be included within the delivery catheter 1 and positioned such that the proximal tips of the sheaths are within the region of the respective fenestrations of the prosthesis in its radially compressed configuration. To this end, when relevant portion of prosthesis is radially expanded, the proximal tips of the catheters 50A, 50B are in position for precannulation, such as shown in FIG. 4.

To this end, the sheath system 50A may be disposed over the guide 31 within the lumen 32 of the prosthesis 20 where the proximal end of sheath 54A is exposed through lateral fenestration 27A. Similarly, the sheath system 50B may be disposed over the guide 31 within the lumen 32 of the prosthesis 20 where the proximal end of sheath 54B is exposed through lateral fenestration 27B. Here, the body portion 31C of the guide 31 may be extended along the side of the tubular graft 18 opposite the anterior fenestration 29, as shown.

Figure 11:
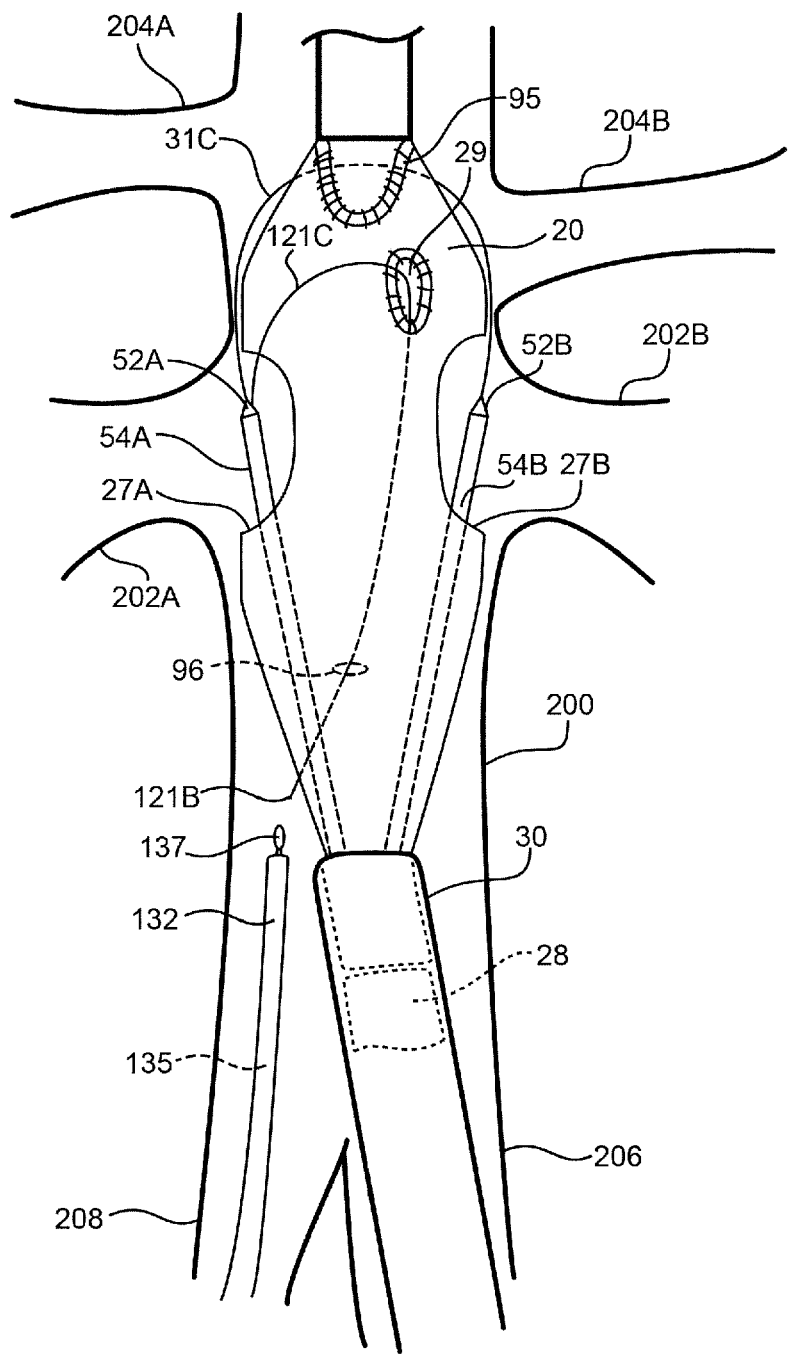

In FIG. 11, the system 2 is shown delivered within an ipsilateral side vessel 206, while a second introducer sheath 132 is delivered within the contralateral side vessel 208. The second introducer sheath 132 can be delivered over a guide wire (not shown) and advanced until the end of the withdrawn sheath 30. A snare device 137 can then be introduced through a lumen 135 of the second introducer sheath 132, and advance to a position to attach to the second wire end 121B of the second guide 120. The snare device 137 can be configured as a retrieval structure such as a loop to capture the second wire end 121B of the second guide 120, or for example, a hook-ended retrieval catheter to capture a loop formed at the second wire end 121B. Once snared or captured, the second wire end 121B of the second guide 120 can be withdrawn distally through the posterior opening 96 and through the second introducer sheath 132 to external the patient or together with the withdrawal of the second introducer sheath 132.

Figure 12:
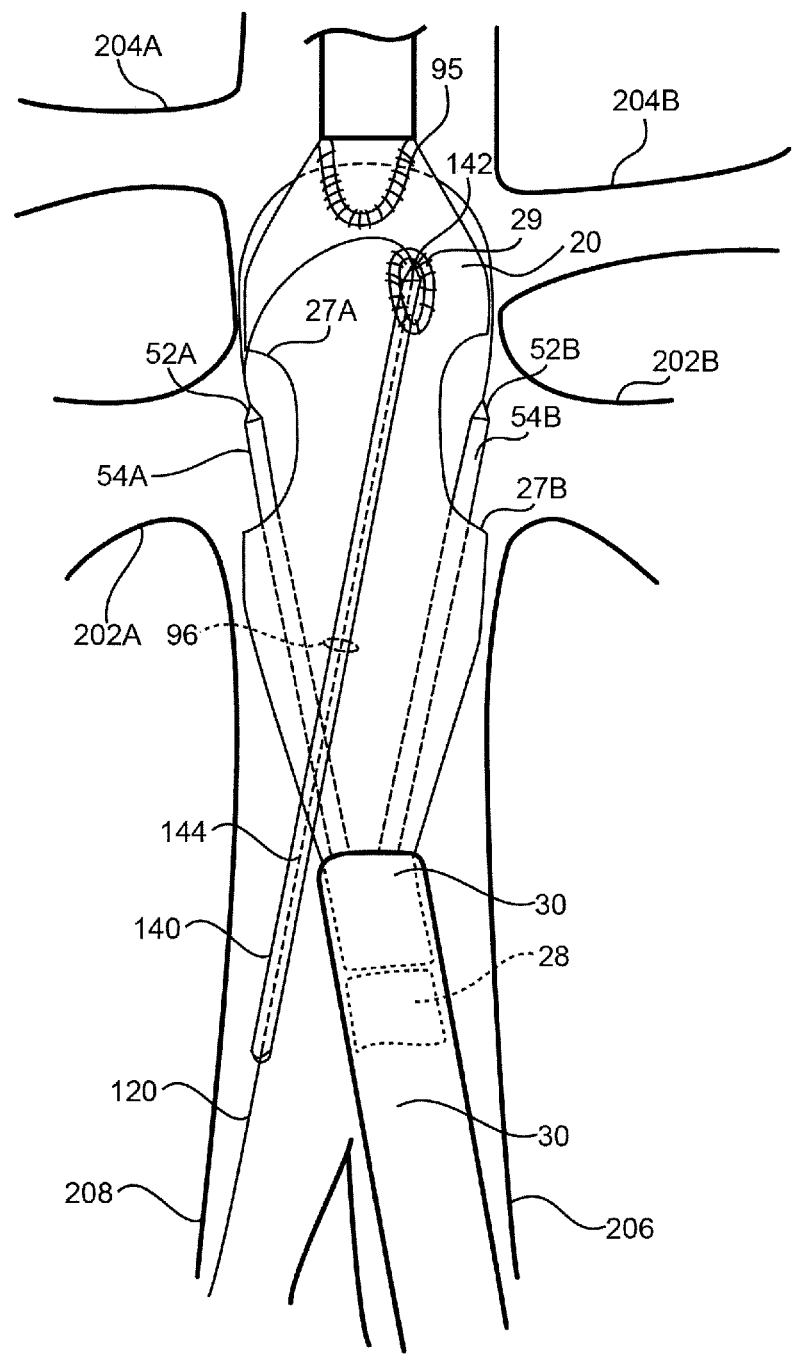

In FIG. 12, an sheath system 140 may be provided and delivered to the prosthesis 20 over the distally retracted second guide 120 at the contralateral side vessel 208. This can occur after the removal of the second introducer sheath 132. In one embodiment, the sheath system 140 can be moved through the axial lumen 135 of the second introducer sheath 132 if left within the body vessel. The sheath system 140 may include, for example, an elongated tubular sheath 144 and an elongated dilator 142, respectively, slidably disposed within an axial lumen of the sheath 144. The second introducer sheath 132 and/or sheath system 140 may also include hemostatic sealing units (not shown), as described above, to limit or prevent blood loss through the respective lumens, and may include side tubes for introducing medical reagents through the respective lumens. The sheath system 140 can then be advanced proximally over the second guide 120, through the posterior opening 96, traversing through the lumen 35 of the prosthesis 20, and out through the anterior fenestration 29. The sheath system 140 may be used to cannulate a target branch vessel 204B through the anterior fenestration 29. The second guide 120 can also be known as a preloaded SMA guide when used to cannulate the SMA branch vessel. In one example, the sheath system 140 is extended through the uncoupled side 102 of the patch 99, when employed, along the underneath side of the patch 99 between the patch and the exterior surface 24 of the prosthesis, into the posterior opening 96, and to the anterior fenestration through the prosthesis lumen 35. In one example, the inner segment 114 of the flap patch 110, when employed, is at its open position to allow communication through the posterior opening 96.

Figure 13:
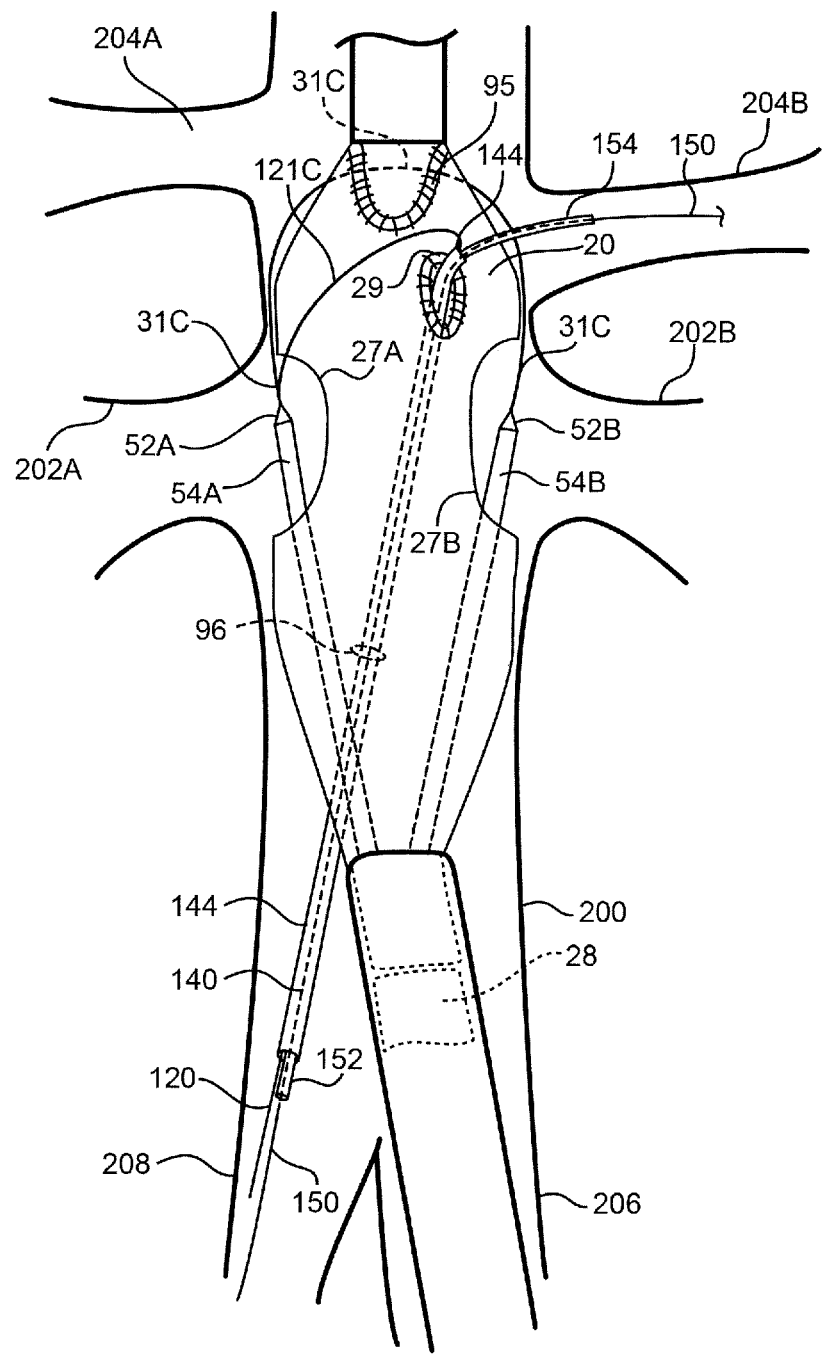

In FIG. 13, the dilator 142 of the sheath system 140 has been removed by withdrawing it distally through the sheath 144. Next, another branch guide wire 150 is provided for cannulating the branch vessel 204B. The branch guide wire 150 can be delivered through the sheath 144 alongside a first end portion of the second guide 120. A branch access catheter 152 can then be introduced over the branch guide wire 150. The branch access catheter 152 may have a steerable proximal end portion 154 that can be used to guide the branch guide wire 150 through the anterior fenestration 29 and farther into the branch vessel 204B. Suitable catheters are commercially available and include the Torcon NB® Advantage Catheters available from Cook Inc., Bloomington, Ind., USA.

Figure 14:
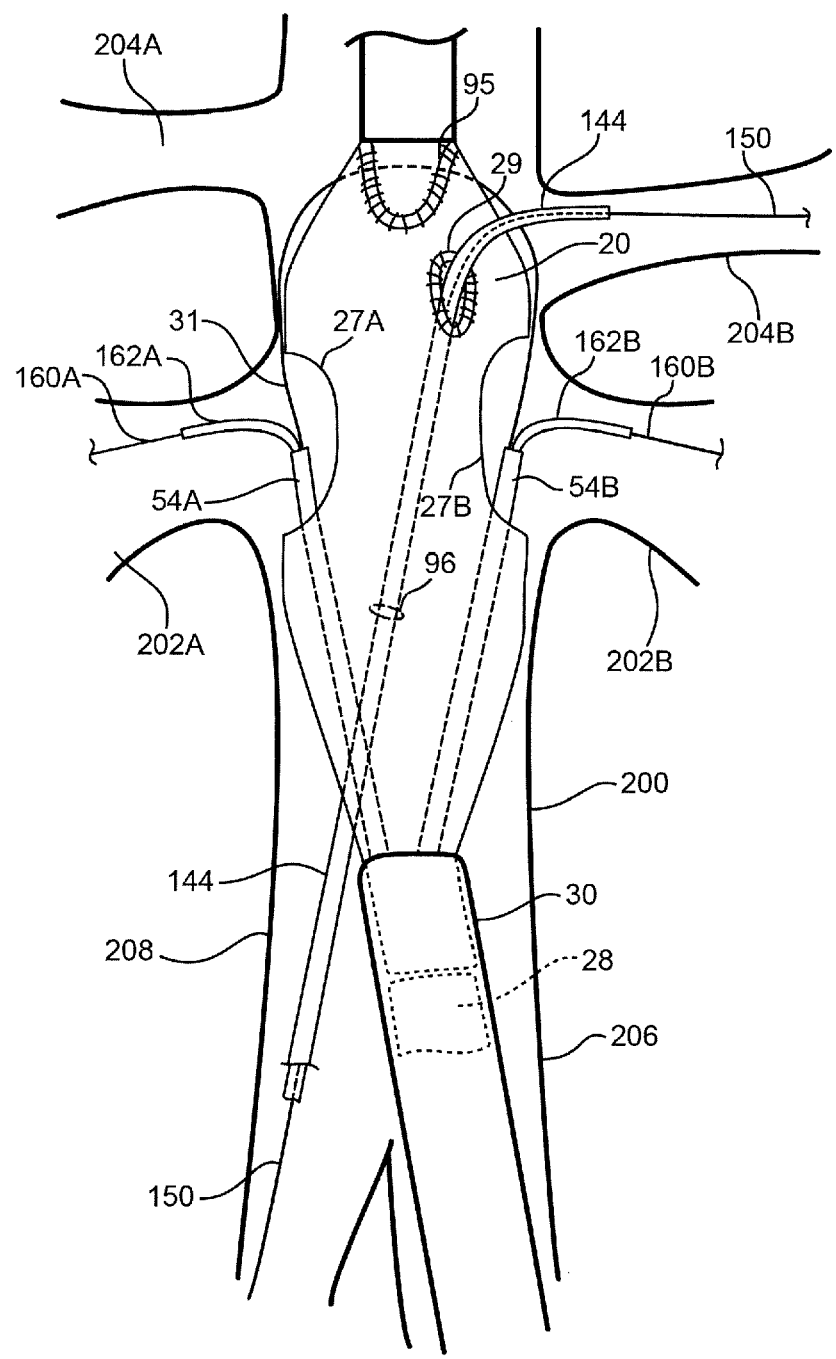

In FIG. 14, once the branch vessel 204B is cannulated, the branch access catheter 152 is removed, by withdrawing it distally through the sheath 144. At this point, the guide 120 is no longer needed and may be removed by pulling distally on the first wire end 121A until the second wire end 121B exits the port 44A, or by pulling distally on the second wire end 121B until the first wire end 121A exits through the distal end opening of the sheath system 140. After removal of the branch access catheter 152, FIG. 14 depicts the sheath 144 being pushed farther into the branch vessel 204B over the branch guide wire 150 in order to provide guidance to the branch vessel for other devices. In one example, the preloaded guide 120 can be removed prior to the branch vessel 204B is cannulated.

In FIG. 14, the dilators 52A, 52B of the sheath systems 50A, 50B have been removed by withdrawing them distally through the sheaths 54A, 54B, respectively. Next, the branch guide wires 160A, 160B are provided for cannulating the branch vessels 202A, 202B. As shown in FIG. 14, the branch guide wire 160A is delivered through the sheath 54A alongside a first end portion of the guide 31 and the branch guide wire 160B is delivered through the sheath 54B alongside a second end portion of the guide 31. The guide 31 can also be known as a preloaded renal guide when used to cannulate at least one of the renal branch vessels. Branch access catheters 162A, 162B are then introduced over the guide wires 160A, 160B, respectively. The branch access catheters 162A, 162B preferably have steerable proximal end portions that can be used to guide the branch guide wires 160A, 160B through the lateral fenestrations 27A, 27B and into respective branch vessels 202A, 202B.

Figure 15:
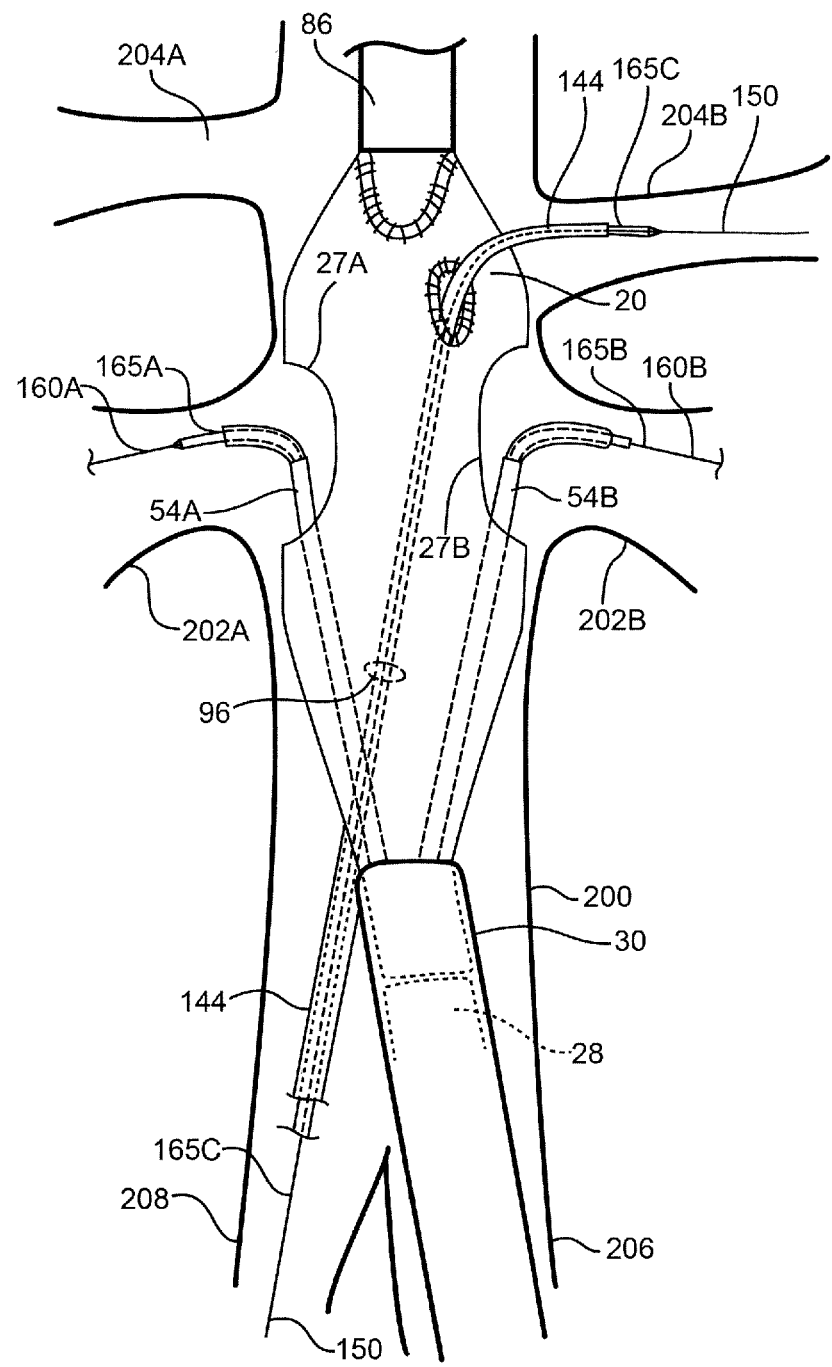

In FIG. 15, once the branch vessels 202A, 202B are cannulated, the branch access catheters 162A, 162B are removed, by withdrawing them distally through the sheaths 54A, 54B. At this point, the preloaded wire 31 is no longer needed and may be removed by pulling distally on the first wire end 31A until the second wire end 31B exits port 44A, or by pulling on the second wire end until the first wire end exits port 44B. After removal of the preloaded wire 31 and the branch access catheter 162A, 162B, the sheaths 54A, 54B can be pushed farther into the branch vessels 202A, 202B over the respective branch guide wires 160A, 160B in order to provide guidance to the branch vessels for other devices.

With the guide wires 150, 160A, 160B in place, the operator may now deliver one or more interventional catheters 165A, 165B, 165C (including, for example, catheters carrying balloons, stents, grafts, imaging devices, and the like) through the respective sheaths 54A, 54B, 144 into the branch vessels 202A, 202B, 204B through the lateral fenestrations 27A, 27B and the anterior fenestration 29, as shown in FIG. 15. In some instances, the top cap 86 can be removed from the proximal outflow end of the prosthesis 20 by sliding the inner cannula 15 coupled to the tapered extension 11 that is coupled to the top cap 86 proximally with respect to the pusher 28. The outer sheath 30 can also be fully retracted from the prosthesis 20, exposing the remaining distal inflow end of prosthesis and allowing it to radially expand for deployment.

After deployment of the prosthesis, the interventional catheters 165A, 165B, 165C are removed, the guide wires 150, 160A, 160B are removed, and the respective sheaths 54A, 54B, 144 are removed from the body. In one example, the sheath 144 is removed from the posterior opening 96, along the underneath side of the patch 99, when employed, between the patch and the exterior side of prosthesis, and through the uncoupled side 102 of the patch 99. The patch 99 is then adapted to seal the posterior opening 96. In one example, the inner segment 114 of the flap patch 110, when employed, is then moved to its closed position to help seal the posterior opening 96.

In one example, the system 2 includes the sheath systems 50A and/or 50B with the second guide 120 positioned during delivery of the system as described herein to allow for precannulation of a branch body vessel, such as the SMA. One benefit of such arrangement is the elimination of manual cannulation following a full retraction of the outer sheath 30 from the prosthesis 20. The sheath systems 50A, 50B (either one or both) can be preloaded at their operable positions within the prosthesis 20. In the context of this disclosure, the term "preloaded" used in association with elements of the prosthesis 20 and the delivery device 2 means that at least a portion of the guide 120, the guide 31, the sheath system 50A, the sheath system 50B, or any combination thereof, is disposed within the lumen 35 of the tubular body 19 of the prosthesis 20 prior the introduction of the delivery device 2 into the patient's body. Hence, the prosthesis 20, a portion of the guide 120 and/or 31, a portion of the sheath systems 50A and/or 50B, depending on which is employed, will be present in the device 2 and enclosed within the outer sheath 30 covering the device 2 prior to any use of the device 2 by a physician. In one example, the system includes both sheath systems 50A, 50B, sized e.g., at 6 Fr, with the first guide 31, sized e.g., at about 0.018 inches, and the second guide 120, sized e.g., at about 0.018 inches, are preloaded at their operable positions within the prosthesis 20 in the radially compressed configuration for delivery, with the proximal tips of the catheters 50A, 50B located at the respective lateral fenestrations 27A, 27B. This can improve the procedure time, among other things, for, not only other branch body vessels, such as renal artery cannulation, but also SMA cannulation, that would be required using manual cannulation or advancing the sheaths during the procedure. In one example, the outer sheath 30 can remain partially withdrawn from the prosthesis 20 during a branch body vessel, such as SMA cannulation, that is, still restraining the distal inflow end of the prosthesis 20, which can facilitate improvement in repositioning and torque control of the prosthesis 20 during cannulation, with minimal graft exposed from the delivery system. Other advantages of the system will be apparent to one of ordinary skill in the art.

The shape, size, and dimensions of each of the members of the prosthesis may vary. The size of the prosthesis 20 is determined primarily by the diameter of the vessel lumen (preferably for a healthy valve/lumen combination) at the intended implant site, as well as the desired length of the overall stent and valve device. The prosthesis may include a distal region having a first cross-sectional area, a proximal region having a second, larger cross-sectional area, and a tapered region disposed between the proximal and distal regions.

The stent described herein is depicted as comprising one or more zig-zag stents. The stent may include shapes other than the zig-zag shape depicted. The term "stent" means any device or structure that provides or is configured to provide rigidity, expansion force, or support to a body part, for example, a diseased, damaged, or otherwise compromised body lumen. A stent may include any suitable biocompatible material, including, but not limited to fabrics, metals, plastics, and the like. Examples of suitable materials include metals such as stainless steel and nitinol, and plastics such as polyethylene terephthalate ("PET"), polytetrafluoroethylene ("PTFE") and polyurethane. A stent may be "expandable," that is, it may be capable of being expanded to a larger-dimension configuration. A stent may expand by virtue of its own resilience (i.e., self-expanding), upon the application of an external force (i.e., balloon-expandable), or by a combination of both. In one example, a stent may have one or more self-expanding portions and one or more balloon-expandable portions. An example of a suitable self-expanding stent includes Z-STENTS®, which are available from Cook Inc., Bloomington, Ind., USA.

The term "graft" describes an object, device, or structure that is joined or that is capable of being joined to a body part to enhance, repair, or replace a portion or a function of that body part. Grafts that can be used to repair body vessels include, for example, films, coatings, or sheets of material that are formed or adapted to conform to the body vessel that is being enhanced, repaired, or replaced. A stent may be attached to or associated with a graft to form a prosthesis or stent-graft. A graft material may include a biocompatible synthetic or biological material. Examples of suitable synthetic materials include fabrics, woven and non-woven materials, and porous and non-porous sheet materials. One exemplary synthetic graft material includes a woven polyester having a twill weave and a porosity of about 350 ml/min/cm·sup.2, and is available from Vascutek Ltd., Inchinnan, Scotland, UK. Other synthetic graft materials include biocompatible materials such as polyester, polytetrafluoroethylene (PTFE), polyurethane, and the like. Examples of suitable biological materials include, for example, pericardial tissue and extracellular matrix materials such as SIS. In one example, low profile graft material is provided, which can be about one-half the thickness of the stent member.

The delivery systems described herein may need various other components in order to obtain a delivery and deployment system that is optimally suited for its intended purpose. These include and are not limited to various outer sheaths, pushers, trigger wires, stoppers, guide wires, and the like. For example, the Zenith® Thoracic Aortic Aneurysm Endovascular Graft uses a delivery system that is commercially available from Cook Inc., Bloomington, Ind., and may be suitable for delivering and deploying an aortic prosthesis in accordance with the present embodiments.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endoluminal prosthesis deployment system, comprising:
    a prosthesis including a support structure coupled to a graft body, the prosthesis having a first end opening, a second end opening, a lumen extending longitudinally between the first and second end openings, an anterior fenestration disposed in a sidewall of the graft body of the prosthesis below the first end opening, at least one lateral fenestration disposed in the sidewall below the anterior fenestration and circumferentially spaced from the anterior fenestration, the at least one lateral fenestration configured to receive a secondary graft, and an opening disposed in the sidewall below the at least one lateral fenestration; and
    a preloaded guide that extends from below the second end opening, extending through the lumen directly to the at least one lateral fenestration, exits through the at least one lateral fenestration and traverses along an exterior surface of the prosthesis extending directly to and through the anterior fenestration from the at least one lateral fenestration and longitudinally along an interior surface of the prosthesis, and extends from the anterior fenestration directly to and out of the opening and away from the opening toward the second end opening of the prosthesis.

2. The system of claim 1, wherein the opening is disposed anteriorly and substantially longitudinally aligned with the anterior fenestration.

3. The system of claim 1, wherein the opening is disposed posteriorly and substantially longitudinally aligned with the anterior fenestration.

4. The system of claim 1, wherein an end of the guide exiting the opening is disposed at a location between the second end opening of the prosthesis and the opening.

5. The system of claim 1, wherein the prosthesis further includes a patch coupled to the sidewall of the graft body of the prosthesis, and disposed to cover the opening.

6. The system of claim 1, wherein the at least one lateral fenestration is a first lateral fenestration, the prosthesis further includes a second lateral fenestration formed in the sidewall and circumferentially spaced from the first lateral fenestration about the prosthesis, wherein the first and second lateral fenestrations are axially arranged in between the anterior fenestration and the opening.

7. The system of claim 6, wherein the guide is a first guide, the system further comprising a second guide, the second guide extending from below the second end opening to the first lateral fenestration, exiting the first lateral fenestration, traversing along the exterior surface of the prosthesis, entering through the second lateral fenestration, and exiting the lumen through the second end opening.

8. The system of claim 7, further comprising a first sheath defining an axial lumen inserted over a first end of the second guide and disposed such that a proximal tip of the first sheath is located within the first lateral fenestration, and a second sheath defining an axial lumen inserted over a second end of the second guide, opposite the first end of the second guide, and disposed such that a proximal tip of the second sheath is located within the second lateral fenestration.

9. The system of claim 8, wherein the axial lumen of the first sheath is disposed over both of a first end of the first guide and the first end of the second guide, wherein both of the first guide and the second guide extend out of the proximal tip of the first sheath.

10. The system of claim 6, further comprising:
    an outer sheath disposed about at least a portion of the guide; and
    a proximal cap,
    wherein the outer sheath is movable from an extended delivery position to a retracted position, where in the extended delivery position the outer sheath and the proximal cap together define a delivery lumen to maintain the prosthesis in a radially compressed configuration.

11. The system of claim 10, wherein the guide is a preloaded first guide, the system further comprising:
    a preloaded second guide extending from below the second end opening to the first lateral fenestration, exiting the first lateral fenestration, traversing along the exterior surface of the prosthesis, entering through the second lateral fenestration, and exiting the lumen through the second end opening; and
    a preloaded first sheath defining an axial lumen inserted over a first end of the preloaded second guide and disposed such that a proximal tip of the first sheath is located within the first lateral fenestration, and a preloaded second sheath defining an axial lumen inserted over a second end of the preloaded second guide, opposite the first end of the preloaded second guide, and disposed such that a proximal tip of the preloaded second sheath is located within the second lateral fenestration,
    wherein, when the outer sheath is in an extended delivery position, the delivery lumen is further configured to maintain the prosthesis in the radially compressed configuration, the preloaded first and second guides, and the preloaded first and second sheaths within the prosthesis lumen.

12. The system of claim 11, wherein the axial lumen of the first sheath is inserted over both of a first end of the first guide and the first end of the second guide.

13. A method for deploying a prosthesis within a main vessel of a patient, having a branch vessel intersecting the main vessel, the method comprising:
    providing a prosthesis having a first end opening, a second end opening, a prosthesis lumen extending longitudinally between the first and second end openings, an anterior fenestration disposed in a sidewall of a graft body of the prosthesis below the first end opening, an opening disposed in the sidewall closer in proximity to the second end opening than the anterior fenestration, and a lateral fenestration disposed in the sidewall in between the anterior fenestration and the opening, and a preloaded guide extending from below the second end opening, then extending through the lumen to the lateral fenestration directly from the second end opening, then exiting the lateral fenestration, then traversing along an exterior surface of the prosthesis, then entering the anterior fenestration directly from the lateral fenestration then longitudinally traversing along an interior surface of the prosthesis, and then exiting the opening directly from the anterior fenestration to extend away from the opening toward the second end opening of the prosthesis;

expanding a portion of the prosthesis that includes the anterior fenestration, the opening, and the lateral fenestration within a main vessel such that the anterior fenestration is in alignment with a branch vessel;

coupling a snare device to an end of the guide exiting the opening; and retracting the end of the guide away from the second end opening of the prosthesis.

14. The method of claim 13, further comprising:

inserting an axial lumen of a sheath over the end of the guide after the retracting step; and sliding the sheath over the retracted guide in a direction toward the prosthesis, through the opening, and traversing along an interior surface of the prosthesis lumen to the anterior fenestration.

15. The method of claim 14, wherein the prosthesis further includes a patch coupled to the sidewall of the graft body of the prosthesis, and disposed to cover the opening, wherein the sliding the sheath step further includes sliding the sheath over the retracted guide in a direction toward the prosthesis, underneath the patch and into the opening, and traversing along an interior surface of the prosthesis lumen to the anterior fenestration.

16. The method of claim 14, further comprising:

maintaining a proximal tip of the sheath outside of the prosthesis lumen at the anterior fenestration; and introducing a branch guide wire through the sheath such that an end of the branch guide wire exits the proximal tip and enters into the branch vessel.

17. The method of claim 16, further comprising:

maintaining the end of the branch guide wire outside the proximal tip and within the branch vessel;

removing the guide from the sheath;

sliding the sheath over the branch guide wire such that the proximal tip is outside the anterior fenestration and farther into the branch vessel; and sliding an interventional catheter through the axial lumen of the auxiliary catheter sheath over the branch guide wire into the branch vessel.

18. An endoluminal prosthesis deployment system, comprising:

a prosthesis having a tubular graft body, the prosthesis having a first axial end opening, a second axial end opening, a lumen extending longitudinally between the first and second axial end openings, a first fenestration defined in a sidewall of the graft body of the prosthesis below the first axial end opening along an anterior circumferential region of the prosthesis; a second fenestration defined in the sidewall below the first fenestration and along a lateral circumferential region circumferentially spaced from the anterior circumferential region, and an opening defined in the sidewall below the second fenestration and along a posterior circumferential region circumferentially spaced from the anterior circumferential region and the lateral circumferential region, wherein the prosthesis includes a patch coupled to the sidewall of the graft body, and disposed to cover the opening; and a preloaded guide that extends from below the second axial end opening extending through the lumen directly to and through the second fenestration to and along an exterior surface of the prosthesis extends directly to and through the first fenestration from the second fenestration into the lumen and longitudinally along an interior surface of the prosthesis, and extends from the first fenestration directly to and out of the opening and away from the opening between the patch and the exterior surface of the prosthesis toward the second axial end opening of the prosthesis.

19. The system of claim 18, wherein an end of the guide exiting the opening is disposed at a location between the second axial end opening of the prosthesis and the opening.

20. The system of claim 18, wherein the lateral circumferential region is a first lateral circumferential region, wherein a third fenestration is defined in the sidewall below the first fenestration and along a second lateral circumferential region circumferentially spaced from the first lateral circumferential region along an axial segment, wherein the guide is a first guide, the system further comprising a second guide extending from below the second axial end opening to the second fenestration, exiting the second fenestration, traversing along the exterior surface of the prosthesis, entering through the third fenestration, and exiting the lumen through the second axial end opening.

21. The system of claim 20, further comprising a preloaded first sheath defining an axial lumen inserted over a first end of the second guide and disposed such that a proximal tip of the preloaded first sheath is located within the second fenestration, and a preloaded second sheath defining an axial lumen inserted over a second end of the second guide, opposite the first end of the second guide, and disposed such that a proximal tip of the preloaded second sheath is located within the third fenestration.

22. The system of claim 21, wherein the axial lumen of the preloaded first sheath is disposed over both of a first end of the first guide and the first end of the second guide, wherein both of the first guide and the second guide extend out of the proximal tip of the preloaded first sheath.

* * * * *